(12) United States Patent
Uth et al.

(10) Patent No.: US 8,758,303 B2
(45) Date of Patent: Jun. 24, 2014

(54) INJECTION PORT WITH APPLIER

(75) Inventors: Joshua Uth, Mason, OH (US); Randal T. Byrum, South Lebanon, OH (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 11 days.

(21) Appl. No.: 12/769,929

(22) Filed: Apr. 29, 2010

(65) Prior Publication Data

US 2010/0217200 A1 Aug. 26, 2010

Related U.S. Application Data

(63) Continuation of application No. 11/166,625, filed on Jun. 24, 2005, which is a continuation-in-part of application No. 10/741,875, filed on Dec. 19, 2003, now Pat. No. 7,862,546.

(60) Provisional application No. 60/478,763, filed on Jun. 16, 2003.

(51) Int. Cl.
*A61M 5/00* (2006.01)

(52) U.S. Cl.
USPC .......................................... 604/175

(58) Field of Classification Search
USPC .......... 604/533–535, 175, 96.01, 164.01, 523
See application file for complete search history.

(56) References Cited

U.S. PATENT DOCUMENTS

| 2,737,954 | A | 3/1956 | Knapp |
| 3,371,352 | A | 3/1968 | Siposs et al. |
| 3,587,115 | A | 6/1971 | Shiley |
| 3,686,740 | A | 8/1972 | Shiley |
| 3,850,324 | A | 11/1974 | Meyer |
| 4,378,023 | A | 3/1983 | Trabucco |
| 4,543,088 | A | 9/1985 | Bootman et al. |
| 4,569,675 | A * | 2/1986 | Prosl et al. ..................... 604/175 |

(Continued)

FOREIGN PATENT DOCUMENTS

| AU | 2004281641 | 5/2010 |
| AU | 2006202145 | 12/2012 |

(Continued)

OTHER PUBLICATIONS

U.S. Appl. No. 60/478,763, filed Jun. 16, 2003, Conlon et al.

(Continued)

*Primary Examiner* — Emily Schnidt
*Assistant Examiner* — Michael J Anderson
(74) *Attorney, Agent, or Firm* — Frost Brown Todd LLC

(57) ABSTRACT

An injection port system comprises an injection port and an applier. The port comprises a body and a plurality of fasteners. The fasteners are integral with the body and are movable from a non-deployed position to a deployed position. The applier comprises a port engagement portion and an actuator. The port engagement portion is configured to selectively engage the port body to selectively retain the port relative to the applier. The actuator is operable to move the fasteners to the deployed position. The applier is also configured to disengage the port engagement portion from the port body to release the port from the applier when the actuator moves the fasteners to the deployed position. The actuator may release the port from the applier by moving a resilient member away from the port body as the actuator also moves the fasteners from the non-deployed position to the deployed position.

17 Claims, 22 Drawing Sheets

(56) References Cited

U.S. PATENT DOCUMENTS

| | | |
|---|---|---|
| 4,592,339 A | 6/1986 | Kuzmak et al. |
| 4,621,640 A | 11/1986 | Mulhollan et al. |
| 4,665,906 A | 5/1987 | Jervis |
| 4,673,394 A | 6/1987 | Fenton, Jr. et al. |
| 4,685,447 A | 8/1987 | Iverson et al. |
| 4,692,146 A | 9/1987 | Hilger |
| 4,704,103 A | 11/1987 | Stober et al. |
| 4,710,174 A | 12/1987 | Moden et al. |
| 4,723,948 A | 2/1988 | Clark et al. |
| 4,732,948 A | 3/1988 | McCready et al. |
| 4,738,023 A | 4/1988 | Fabris |
| 4,738,657 A | 4/1988 | Hancock et al. |
| 4,762,517 A | 8/1988 | Mcintyre et al. |
| 4,767,410 A | 8/1988 | Moden et al. |
| 4,772,261 A | 9/1988 | Von Hoff et al. |
| 4,772,270 A | 9/1988 | Wiita et al. |
| 4,778,452 A | 10/1988 | Moden et al. |
| 4,781,680 A | 11/1988 | Redmond et al. |
| 4,781,695 A | 11/1988 | Dalton |
| 4,798,584 A | 1/1989 | Hancock et al. |
| 4,802,885 A | 2/1989 | Weeks et al. |
| 4,834,720 A | 5/1989 | Blinkhorn |
| 4,840,615 A | 6/1989 | Hancock et al. |
| 4,861,341 A | 8/1989 | Woodburn |
| 4,880,414 A | 11/1989 | Whipple |
| 4,892,518 A | 1/1990 | Cupp et al. |
| 4,898,585 A | 2/1990 | Borsanyi et al. |
| 4,904,241 A | 2/1990 | Bark |
| 4,925,445 A | 5/1990 | Sakamoto et al. |
| 4,929,230 A | 5/1990 | Pfleger |
| 4,929,236 A | 5/1990 | Sampson |
| 4,969,873 A | 11/1990 | Steinbach et al. |
| 4,976,715 A | 12/1990 | Bays et al. |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melskky et al. |
| 5,053,013 A | 10/1991 | Ensminger et al. |
| 5,090,954 A | 2/1992 | Geary |
| 5,108,377 A | 4/1992 | Cone et al. |
| 5,123,199 A | 6/1992 | Lysohir et al. |
| 5,129,891 A | 7/1992 | Young |
| 5,133,753 A | 7/1992 | Bark et al. |
| 5,137,529 A | 8/1992 | Watson et al. |
| 5,158,547 A | 10/1992 | Doan et al. |
| 5,174,487 A | 12/1992 | Rothfuss et al. |
| 5,178,612 A | 1/1993 | Fenton, Jr. |
| 5,185,003 A | 2/1993 | Brethauer |
| 5,203,864 A | 4/1993 | Phillips |
| 5,207,644 A | 5/1993 | Strecker |
| 5,213,574 A | 5/1993 | Tucker |
| 5,217,486 A | 6/1993 | Rice et al. |
| 5,226,429 A | 7/1993 | Kuzmak |
| 5,246,156 A | 9/1993 | Rothfuss et al. |
| 5,261,914 A | 11/1993 | Warren |
| 5,263,930 A | 11/1993 | Ensminger |
| 5,279,564 A | 1/1994 | Taylor |
| 5,281,199 A | 1/1994 | Ensminger et al. |
| 5,290,297 A | 3/1994 | Phillips |
| 5,305,202 A | 4/1994 | Gallant et al. |
| 5,318,545 A | 6/1994 | Tucker |
| 5,324,518 A | 6/1994 | Orth et al. |
| 5,328,465 A | 7/1994 | Kratoska et al. |
| 5,332,398 A | 7/1994 | Miller et al. |
| 5,333,772 A | 8/1994 | Rothfuss et al. |
| 5,336,194 A | 8/1994 | Polaschegg |
| 5,350,360 A | 9/1994 | Ensminger et al. |
| 5,360,407 A | 11/1994 | Leonard et al. |
| 5,364,408 A | 11/1994 | Gordon |
| 5,381,943 A | 1/1995 | Allen et al. |
| 5,387,192 A | 2/1995 | Glantz et al. |
| 5,399,168 A | 3/1995 | Wadsworth, Jr. et al. |
| 5,417,656 A | 5/1995 | Ensminger et al. |
| 5,423,857 A | 6/1995 | Rosenman et al. |
| 5,445,616 A | 8/1995 | Kratoska et al. |
| 5,464,407 A | 11/1995 | McGuire |
| 5,470,010 A | 11/1995 | Rothfuss et al. |
| 5,476,460 A | 12/1995 | Montalvo |
| 5,503,630 A | 4/1996 | Ensminger et al. |
| 5,527,277 A | 6/1996 | Ensminger et al. |
| 5,527,278 A | 6/1996 | Ensminger et al. |
| 5,527,321 A | 6/1996 | Hinchliffe |
| 5,540,648 A | 7/1996 | Yoon |
| 5,545,152 A | 8/1996 | Funderburk et al. |
| 5,558,641 A | 9/1996 | Glantz et al. |
| 5,562,618 A | 10/1996 | Cai et al. |
| 5,573,540 A | 11/1996 | Yoon |
| 5,582,616 A | 12/1996 | Bolduc et al. |
| 5,588,581 A | 12/1996 | Conlon et al. |
| 5,591,143 A | 1/1997 | Trombley, III et al. |
| 5,601,224 A | 2/1997 | Bishop et al. |
| 5,601,604 A | 2/1997 | Vincent |
| 5,602,224 A | 2/1997 | Vrckovnik et al. |
| 5,613,945 A | 3/1997 | Cai et al. |
| 5,632,729 A | 5/1997 | Cai et al. |
| 5,634,584 A | 6/1997 | Okorocha et al. |
| 5,635,718 A | 6/1997 | De Puydt et al. |
| 5,637,102 A * | 6/1997 | Tolkoff et al. ................ 604/536 |
| 5,653,718 A * | 8/1997 | Yoon ............................. 606/148 |
| 5,681,330 A | 10/1997 | Hughett et al. |
| 5,683,447 A | 11/1997 | Bush et al. |
| 5,688,247 A | 11/1997 | Haindl et al. |
| 5,700,272 A | 12/1997 | Gordon et al. |
| 5,716,370 A | 2/1998 | Williamson, IV et al. |
| 5,718,682 A | 2/1998 | Tucker |
| 5,743,873 A | 4/1998 | Cai et al. |
| 5,792,104 A | 8/1998 | Speckman et al. |
| 5,792,123 A * | 8/1998 | Ensminger .................... 604/272 |
| 5,810,882 A | 9/1998 | Bolduc et al. |
| 5,817,062 A | 10/1998 | Flom et al. |
| 5,829,662 A | 11/1998 | Allen et al. |
| 5,830,221 A | 11/1998 | Stein et al. |
| 5,853,394 A | 12/1998 | Tolkoff et al. |
| 5,871,532 A | 2/1999 | Schroeppel |
| RE36,176 E | 3/1999 | Kuzmak |
| 5,902,598 A | 5/1999 | Chen et al. |
| 5,954,687 A | 9/1999 | Baudino |
| 5,976,159 A | 11/1999 | Bolduc et al. |
| 5,989,216 A | 11/1999 | Johnson et al. |
| 6,001,386 A | 12/1999 | Ashton et al. |
| 6,086,555 A | 7/2000 | Eliasen et al. |
| 6,102,922 A | 8/2000 | Jakobsson et al. |
| 6,213,973 B1 | 4/2001 | Eliasen et al. |
| 6,251,090 B1 | 6/2001 | Avery et al. |
| 6,290,702 B1 | 9/2001 | Fucci et al. |
| 6,319,226 B1 | 11/2001 | Sherry |
| 6,447,524 B1 | 9/2002 | Knodel et al. |
| 6,461,292 B1 | 10/2002 | Forsell |
| 6,470,892 B1 | 10/2002 | Forsell |
| 6,478,783 B1 | 11/2002 | Moorehead |
| 6,511,490 B2 | 1/2003 | Robert |
| 6,527,754 B1 | 3/2003 | Tallarida et al. |
| 6,540,717 B2 | 4/2003 | Sherry |
| 6,556,857 B1 | 4/2003 | Estes et al. |
| 6,592,571 B1 | 7/2003 | Verbeek et al. |
| 6,607,504 B2 | 8/2003 | Haarala et al. |
| 6,827,722 B1 | 12/2004 | Schoenefeld |
| 6,962,577 B2 | 11/2005 | Tallarida et al. |
| 6,976,159 B1 | 12/2005 | Poduska et al. |
| 6,988,987 B2 | 1/2006 | Ishikawa et al. |
| 7,033,335 B2 | 4/2006 | Haarala et al. |
| 7,076,309 B2 | 7/2006 | Hine et al. |
| 7,097,770 B2 | 8/2006 | Lysenko et al. |
| 7,138,179 B2 | 11/2006 | Kim et al. |
| 7,152,601 B2 | 12/2006 | Barakat et al. |
| 7,152,926 B2 | 12/2006 | Wrobel |
| 7,195,774 B2 | 3/2007 | Carvalho et al. |
| 7,223,239 B2 | 5/2007 | Schulze et al. |
| 7,241,632 B2 | 7/2007 | Yang |
| 7,341,577 B2 | 3/2008 | Gill |
| 7,374,557 B2 | 5/2008 | Conlon et al. |
| 7,387,635 B2 | 6/2008 | Keller |

(56) References Cited

U.S. PATENT DOCUMENTS

| | | |
|---|---|---|
| 7,442,165 B2 | 10/2008 | Forsell |
| 7,553,298 B2 | 6/2009 | Hunt et al. |
| 7,561,916 B2 | 7/2009 | Hunt et al. |
| 7,608,080 B2 | 10/2009 | Shipp et al. |
| 7,651,483 B2 | 1/2010 | Byrum et al. |
| 8,007,479 B2 | 8/2011 | Birk et al. |
| 8,007,747 B2 | 8/2011 | Giter et al. |
| 8,029,477 B2 | 10/2011 | Byrum et al. |
| 8,079,989 B2 | 12/2011 | Birk et al. |
| 8,162,897 B2 | 4/2012 | Byrum |
| 8,211,127 B2 | 7/2012 | Uth et al. |
| 2003/0105385 A1 | 6/2003 | Forsell |
| 2003/0181890 A1 | 9/2003 | Schulze et al. |
| 2004/0068233 A1 | 4/2004 | DiMatteo |
| 2004/0093056 A1 | 5/2004 | Johnson et al. |
| 2004/0199129 A1 | 10/2004 | DiMatteo |
| 2004/0220682 A1 | 11/2004 | Levine et al. |
| 2004/0243195 A1 | 12/2004 | Imran et al. |
| 2004/0249362 A1 | 12/2004 | Levine et al. |
| 2004/0254537 A1 | 12/2004 | Conlon et al. |
| 2005/0131352 A1 | 6/2005 | Conlon et al. |
| 2005/0148956 A1 | 7/2005 | Conlon et al. |
| 2005/0277899 A1 | 12/2005 | Conlon et al. |
| 2005/0283118 A1 | 12/2005 | Uth et al. |
| 2005/0283119 A1 | 12/2005 | Uth et al. |
| 2006/0178647 A1* | 8/2006 | Stats .................. 604/288.01 |
| 2006/0190039 A1 | 8/2006 | Birk et al. |
| 2006/0217668 A1 | 9/2006 | Schulze et al. |
| 2006/0217673 A1 | 9/2006 | Schulze et al. |
| 2006/0234445 A1 | 10/2006 | Yang |
| 2006/0293626 A1 | 12/2006 | Byrum et al. |
| 2007/0185462 A1 | 8/2007 | Byrum |
| 2007/0208313 A1 | 9/2007 | Conlon et al. |
| 2007/0255306 A1* | 11/2007 | Conlon et al. .................. 606/192 |
| 2007/0293823 A1 | 12/2007 | Sherry |
| 2007/0293829 A1 | 12/2007 | Conlon et al. |
| 2010/0217199 A1 | 8/2010 | Uth et al. |
| 2010/0234808 A1 | 9/2010 | Uth et al. |
| 2010/0286649 A1 | 11/2010 | Birk et al. |
| 2011/0082426 A1 | 4/2011 | Conlon et al. |
| 2011/0152901 A1 | 6/2011 | Woodruff et al. |

FOREIGN PATENT DOCUMENTS

| | | |
|---|---|---|
| CN | 1600281 A | 3/2005 |
| DE | 42 11 045 | 10/1993 |
| DE | 197 45 654 | 4/1999 |
| DE | 197 51 791 | 5/1999 |
| EP | 0 858 814 | 8/1998 |
| EP | 1 057 457 | 12/2000 |
| EP | 1 346 753 | 9/2003 |
| EP | 1 488 824 | 12/2004 |
| EP | 1 662 971 | 6/2006 |
| EP | 1 670 362 | 6/2006 |
| EP | 1 676 527 | 7/2006 |
| EP | 1 704 891 | 9/2006 |
| EP | 1 736 123 | 12/2006 |
| EP | 1 736 197 | 12/2006 |
| EP | 1 736 198 | 12/2006 |
| EP | 1 832 252 | 9/2007 |
| JP | 62-281966 | 12/1987 |
| JP | 2-119877 | 5/1990 |
| JP | 03-275075 | 12/1991 |
| JP | 8-107934 | 4/1996 |
| JP | 2000-093524 | 4/2000 |
| JP | 2005-007171 | 1/2005 |
| JP | 2007-505696 | 3/2007 |
| RU | 1823791 | 6/1993 |
| RU | 1823791 | 11/2006 |
| WO | WO 94/22520 | 10/1994 |
| WO | WO 96/40357 | 12/1996 |
| WO | WO 97/01370 | 1/1997 |
| WO | WO 97/30659 | 8/1997 |
| WO | WO 99/26543 | 6/1999 |
| WO | WO 99/34859 | 7/1999 |
| WO | WO 00/33901 | 6/2000 |
| WO | WO 01/80926 | 11/2001 |
| WO | WO 02/053220 | 7/2002 |
| WO | WO 02/743810 | 9/2002 |
| WO | WO 2004/026152 | 4/2004 |
| WO | WO 2005/037055 | 4/2005 |
| WO | WO 2005/072627 | 8/2005 |

OTHER PUBLICATIONS

U.S. Appl. No. 60/503,074, filed Sep. 15, 2003, Birk et al.
Australian Search Report dated Aug. 31, 2007 for Application No. SG200604149-5.
Australian Search Report and Written Opinion dated Nov. 20, 2007 for Application No. SG200604066.
EPO Search Report dated Aug. 19, 2004 for Application No. 04253581.
EPO Search Report dated Oct. 4, 2005 for Application No. 05253363.
EPO Search Report dated Oct. 13, 2006 for Application No. 06253285.
EPO Search Report dated Oct. 16, 2006 for Application No. 06253284.
EPO Search Report dated Oct. 4, 2006 for Application No. 06253285.
Partial EPO Search Report dated Oct. 11, 2006 for Application No. 06253276.
Examination Report dated Nov. 24, 2006 for Application No. 04253581.
Extended EPO Search Report dated Jan. 16, 2007 for Application No. 06253276.
Examination Report dated Oct. 22, 2007 for Application No. 04253581.
Examination Report dated Jan. 18, 2008 for Application No. 05253363.
Examination Report dated Jul. 10, 2008 for Application No. 05253363.
Examination Report dated Jan. 15, 2009 for Application No. 04253581.
European Search Report dated Nov. 17, 2006 for Application No. 06253284.
Opposition Decision from the European Patent Office dated Feb. 4, 2011 for Application No. EP 06253277.
Response in Appeal of Opposition Decision from the European Patent Office dated Nov. 8, 2011 for Application No. EP 06253277.
Examination Report dated Nov. 30, 2006 for Application No. 05253363.
Australian Search Report dated Sep. 7, 2007 for Singaporean Application No. SG206604149.
Australian Written Opinion dated Nov. 30, 2007 for Singaporean Application No. SG200604066.
Australian Search Report dated Jul. 16, 2007 for Singaporean Application No. SG200604063.
Australian Examiner's Report dated Apr. 22, 2010 for Application No. AU2005202292.
Australian Examiner's Report Mar. 19, 2012 for Application No. AU 2006202145.
Japanese Office Action dated Dec. 24, 2010 for Application No. JP 2005-160203.
Abstract and English Machine Translation of Japanese Patent No. JP 2000-093524.
Office Action dated Dec. 27, 2010 for U.S. Appl. No. 11/471,767.
Office Action dated Jun. 9, 2011 for U.S. Appl. No. 11/471,767.
Notice of Allowance dated Sep. 21, 2011 for U.S. Appl. No. 11/471,767.
Notice of Allowance dated Jan. 27, 2012 for U.S. Appl. No. 11/471,767.
Notice of Allowance dated Jul. 11, 2012 for U.S. Appl. No. 12/770,047.
Restriction Requirement dated Jun. 24, 2011 for U.S. Appl. No. 12/769,890.
Office Action dated Aug. 15, 2011 for U.S. Appl. No. 12/769,890.
Office Action dated Apr. 5, 2011 for U.S. Appl. No. 12/769,914.
Office Action dated Oct. 4, 2011 for U.S. Appl. No. 12/769,914.

(56) References Cited

OTHER PUBLICATIONS

Restriction Requirement dated Aug. 28, 2006 for U.S. Appl. No. 10/741,875.
Office Action dated Nov. 2, 2006 for U.S. Appl. No. 10/741,875.
Office Action dated Jun. 25, 2007 for U.S. Appl. No. 10/741,875.
Office Action dated Dec. 17, 2007 for U.S. Appl. No. 10/741,875.
Office Action dated May 27, 2008 for U.S. Appl. No. 10/741,875.
Office Action dated Oct. 27, 2008 for U.S. Appl. No. 10/741,875.
Office Action dated Mar. 20, 2009 for U.S. Appl. No. 10/741,875.
Office Action dated Oct. 2, 2009 for U.S. Appl. No. 10/741,875.
Notice of Allowance dated Apr. 9, 2010 for U.S. Appl. No. 10/741,875.
Notice of Allowance dated Sep. 1, 2010 for U.S. Appl. No. 10/741,875.
Office Action dated May 16, 2007 for U.S. Appl. No. 11/166,625.
Office Action dated Oct. 22, 2007 for U.S. Appl. No. 11/166,625.
Office Action dated Jan. 14, 2008 for U.S. Appl. No. 11/166,625.
Office Action dated Jul. 23, 2008 for U.S. Appl. No. 11/166,625.
Office Action dated Mar. 20, 2009 for U.S. Appl. No. 11/166,625.
Office Action dated Sep. 3, 2009 for U.S. Appl. No. 11/166,625.
Office Action dated Mar. 19, 2010 for U.S. Appl. No. 11/166,625.
Office Action dated Mar. 29, 2011 for U.S. Appl. No. 11/166,625.
Notice of Allowance dated May 16, 2011 for U.S. Appl. No. 11/166,625.
Office Action dated Apr. 12, 2007 for U.S. Appl. No. 11/166,610.
Office Action dated Oct. 17, 2007 for U.S. Appl. No. 11/166,610.
Office Action dated Jan. 15, 2008 for U.S. Appl. No. 11/166,610.
Office Action dated Jul. 14, 2008 for U.S. Appl. No. 11/166,610.
Office Action dated Dec. 29, 2008 for U.S. Appl. No. 11/166,610.
Office Action dated Jun. 3, 2009 for U.S. Appl. No. 11/166,610.
Notice of Allowance dated Jan. 15, 2010 for U.S. Appl. No. 11/166,610.
Notice of Allowance dated Feb. 1, 2010 for U.S. Appl. No. 11/166,610.
Notice of Allowance dated Sep. 7, 2010 for U.S. Appl. No. 11/166,610.
Restriction Requirement dated Nov. 27, 2006 for U.S. Appl. No. 10/741,868.
Office Action dated Mar. 7, 2007 for U.S. Appl. No. 10/741,868.
Office Action dated Sep. 7, 2007 for U.S. Appl. No. 10/741,868.
Notice of Allowance dated Jan. 14, 2008 for U.S. Appl. No. 10/741,868.
Office Action dated Feb. 27, 2008 for U.S. Appl. No. 11/166,611.
Office Action dated Jul. 31, 2008 for U.S. Appl. No. 11/166,611.
Office Action dated Oct. 20, 2008 for U.S. Appl. No. 11/166,611.
Notice of Allowance dated May 19, 2009 for U.S. Appl. No. 11/166,611.
Notice of Allowance dated Sep. 25, 2009 for U.S. Appl. No. 11/166,611.
Office Action dated Aug. 15, 2007 for U.S. Appl. No. 11/166,283.
Office Action dated Jan. 8, 2008 for U.S. Appl. No. 11/166,283.
Notice of Allowance dated Jun. 17, 2008 for U.S. Appl. No. 11/166,283.
Notice of Allowance dated Nov. 3, 2008 for U.S. Appl. No. 11/166,283.
Notice of Allowance dated Mar. 4, 2009 for U.S. Appl. No. 11/166,283.
Office Action dated Aug. 10, 2007 for U.S. Appl. No. 11/166,702.
Office Action dated Jan. 8, 2008 for U.S. Appl. No. 11/166,702.
Office Action dated Sep. 25, 2008 for U.S. Appl. No. 11/166,702.
Office Action dated Feb. 13, 2009 for U.S. Appl. No. 11/166,702.
Office Action dated May 14, 2009 for U.S. Appl. No. 11/166,702.
Office Action dated Dec. 4, 2009 for U.S. Appl. No. 11/166,702.
Office Action dated Jun. 7, 2010 for U.S. Appl. No. 11/166,702.
Notice of Allowance dated Dec. 13, 2010 for U.S. Appl. No. 11/166,702.
Office Action dated Jul. 23, 2007 for U.S. Appl. No. 11/166,968.
Restriction Requirement dated Jan. 2, 2008 for U.S. Appl. No. 11/166,968.
Office Action dated Apr. 18, 2008 for U.S. Appl. No. 11/166,968.
Office Action dated Sep. 8, 2008 for U.S. Appl. No. 11/166,968.
Restriction Requirement dated Feb. 13, 2009 for U.S. Appl. No. 11/166,968.
Notice of Allowance dated Apr. 6, 2009 for U.S. Appl. No. 11/166,968.
Office Action dated Jul. 12, 2007 for U.S. Appl. No. 10/858,614.
Office Action dated Nov. 14, 2007 for U.S. Appl. No. 10/858,614.
Office Action dated Mar. 31, 2008 for U.S. Appl. No. 10/858,614.
Office Action dated Nov. 13, 2008 for U.S. Appl. No. 10/858,614.
Office Action dated Apr. 15, 2009 for U.S. Appl. No. 10/858,614.
Office Action dated Oct. 27, 2009 for U.S. Appl. No. 10/858,614.
Office Action dated Mar. 28, 2007 for U.S. Appl. No. 10/741,127.
Office Action dated Sep. 11, 2007 for U.S. Appl. No. 10/741,127.
Office Action dated Jan. 8, 2008 for U.S. Appl. No. 10/741,127.
Office Action dated Jul. 7, 2008 for U.S. Appl. No. 10/741,127.
EPO Notice of Opposition to a European Patent dated Sep. 2, 2009 for European Application No. and Patent No. 06 253 277.5 / 1 736 197.
EPO Response to Attend Oral Proceedings dated Nov. 8, 2010 for European Application No. and Patent No. 06 253 277.5 / 1 736 197.
Russian Office Action for Application No. RU 2006122624/14 (024565).
European Search Report dated Apr. 26, 2011 for Application No. 10177441.
European Search Report dated Mar. 31, 2011 for Application No. 10177808.
European Search Report dated Oct. 4, 2006 for Application No. 06253277.
European Search Report dated Oct. 18, 2007 for Application No. 07252500.
Partial European Search Report dated Sep. 27, 2006 for Application No. 06253283.
Partial European Search Report dated Aug. 4, 2009 for Application No. 08251093.
EPO Notice of Opposition to a European Patent dated Sep. 2, 2009 for European Application No. and Patent No. 06 253 277.5/1 736 197.
EPO Response to Attend Oral Proceedings dated Nov. 8, 2010 for European Application No. and Patent No. 06 253 277.5/1 736 197.
European Examination report dated Mar. 4, 2009 for Application No. 06 253 283.3.
Australian Examiner's Report dated Feb. 25, 2011 for Application No. AU 2006202145.
Australian Examiner's Report dated Jun. 2, 2009 for Application No. AU 2004202549.
Australian Examiner's Report dated Feb. 18, 2011 for Application No. AU 2006202115.
Australian Examiner's Report dated Sep. 27, 2011 for Application No. AU 2011200887.
Australian Examiner's Report dated Dec. 21, 2011 for Application No. AU 2011200887.
Australian Examiner's Report dated Apr. 18, 2012 for Application No. AU 2007202311.
Canadian Office Action dated Apr. 11, 2011 for Application No. CA 2471185.
Canadian Office Action dated Nov. 9, 2011 for Application No. CA 2508648.
Canadian Office Action dated Sep. 19, 2012 for Application No. CA 2508648.
Canadian Office Action dated Nov. 7, 2012 for Application No. CA 2549219.
Canadian Office Action dated Nov. 6, 2012 for Application No. CA 2549241.
Canadian Office Action dated Mar. 19, 2013 for Application No. CA 2590827.
Chinese Office Action dated Apr. 20, 2007 for Application No. CN 200410069447.0.
Chinese Office Action dated Jan. 12, 2012 for Application No. CN 200610093155X.
Chinese Office Action dated Dec. 22, 2011 for Application No. CN 200610093156.4.
Chinese Office Action dated Apr. 19, 2012 for Application No. CN 200610093156.4.
Chinese Office Action dated Jun. 22, 2010 for Application No. CN 200710112538.1.

(56) References Cited

OTHER PUBLICATIONS

Chinese Office Action dated Jul. 6, 2011 for Application No. CN 200710112538.1.
Chinese Office Action dated Apr. 5, 2012 for Application No. CN 200710112538.1.
Israeli Office Action dated Dec. 8, 2009 for Application No. IL 175828.
Israeli Office Action dated Dec. 14, 2009 for Application No. IL 175851.
Japanese Office Action dated Nov. 8, 2011 for Application No. JP 2005-160203.
Japanese Office Action dated Dec. 14, 2006 for Application No. JP 2004-177065.
Japanese Office Action dated Jun. 25, 2010 for Application No. JP 2004-177065.
Japanese Office Action dated Feb. 23, 2011 for Application No. JP 2004-177065.
Japanese Office Action dated Sep. 29, 2011 for Application No. JP 2006-174158.
Japanese Office Action dated Apr. 25, 2011 for Application No. JP 2006-174171.
Japanese Office Action dated Jun. 8, 2012 for Application No. JP 2007-162956.
Japanese Office Action dated Feb. 28, 2013 for Application No. JP 2007-162956.
Korean Office Action dated Oct. 21, 2011 for Application No. KR 10-2005-0045990.
Korean Office Action dated Dec. 18, 2012 for Application No. KR 10-2006-0056843.
Korean Office Action dated Dec. 19, 2012 for Application No. KR 10-2006-0056844.
Mexican Office Action dated Mar. 30, 2007 for Application No. PA/A/2004/005756.
Mexican Office Action dated May 14, 2009 for Application No. PA/A/2006/007379.
Mexican Office Action dated Nov. 20, 2009 for Application No. PA/A/2006/007379.
Mexican Office Action dated Nov. 7, 2011 for Application No. PA/A/2005/005810.
Mexican Office Action dated Oct. 16, 2009 for Application No. MX/A/2007/007468.
Russian Office Action dated May 20, 2009 for Application No. RU 2005116666.
Russian Office Action dated Apr. 28, 2010 for Application No. RU 2006122615.
Singaporean Office Action dated Oct. 31, 2007 for Application No. SG 200604117-2.
USPTO Notice of Allowance dated Mar. 6, 2013 for U.S. Appl. No. 12/966,236.
Australian Examiner's Report dated May 17, 2013 for Application No. AU 2012254952.
Canadian Office Action dated May 22, 2013 for Application No. CA 2508648.
Japanese Office Action dated Aug. 6, 2013 for Application No. JP 2007-162956.
Notice of Allowance dated Sep. 18, 2013 for U.S. Appl. No. 12/966,236.
Office Action Final dated Sep. 30, 2013 for U.S. Appl. No. 12/769,914.
U.S. Appl. No. 12/769,883, filed Apr. 29, 2010.

* cited by examiner

INJECTION PORT WITH APPLIER

This application is a continuation of U.S. patent application Ser. No. 11/166,625, filed Jun. 24, 2005, entitled "Implantable Medical Device with Reversible Attachment Mechanism and Method," published as U.S. Pub. No. 2005/0283119, which is a continuation-in-part of U.S. patent application Ser. No. 10/741,875, filed Dec. 19, 2003, entitled "Subcutaneous Self Attaching Injection Port with Integral Moveable Retention Members," published as U.S. Pub. No. 2004/0254537, which claims priority to U.S. Provisional Patent Application Ser. No. 60/478,763, filed Jun. 16, 2003, entitled "Fluid Injection Port for Adjustable Gastric Band." The disclosure of each of those three patent applications is incorporated by reference herein.

This application also incorporates by reference the following U.S. patent applications, both of which were filed on Dec. 19, 2003: application Ser. No. 10/741,127, entitled "Subcutaneous Injection Port for Applied Fasteners," published as U.S. Pub. No. 2005/0131352; and application Ser. No. 10/741,868, entitled "Subcutaneous Self Attaching Injection Port with Integral Fasteners," issued as U.S. Pat. No. 7,374,557.

TECHNICAL FIELD

The present invention relates generally to medical implants and appliers therefor, and more particularly to an attachment mechanism for use with a variety of medical implants and appliers for attaching such medical implants to body tissue. The invention will be disclosed in connection with, but not limited to, surgically implantable injection ports and an applier therefor.

BACKGROUND

Implantable medical devices are typically implanted in a patient to perform a therapeutic function for that patient. Non-limiting examples of such devices include pace makers, vascular access ports, injection ports (such as used with gastric bands) and gastric pacing devices. Such implants need to be attached, typically subcutaneously, in an appropriate place in order to function properly. It is desirable that the procedure to implant such devices be quick, easy and efficient. In many instances it would be beneficial if the surgeon could remove or reposition the device quickly, easily and efficiently.

Injection ports are placed beneath the skin of a body for injecting fluids into the body, such as for infusing medication, blood draws, and many other applications, including adjustable gastric bands. Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

In addition to a latched position to set the outer diameter of the gastric band, adjustability of gastric bands is generally achieved with an inwardly directed inflatable balloon, similar to a blood pressure cuff, into which fluid, such as saline, is injected through a fluid injection port to achieve a desired diameter. Since adjustable gastric bands may remain in the patient for long periods of time, the fluid injection port is typically installed subcutaneously to avoid infection, for instance in front of the sternum. Adjusting the amount of fluid in the adjustable gastric band is achieved by inserting a Huber needle through the skin into a silicon septum of the injection port. Once the needle is removed, the septum seals against the hole by virtue of compressive load generated by the septum. A flexible conduit communicates between the injection port and the adjustable gastric band.

The present invention encompasses an attachment mechanism to secure an medical implant device to body tissue quickly and easily. The attachment mechanism may be reversible, allowing the implantable medical device to be detached quickly and easily for repositioning or removal. Although standard, commercially available instruments may be used to actuate the attachment mechanism, the present invention also encompasses an applier for locating an implantable medical device in the desired location and quickly and easily actuating the attachment mechanism to secure the implantable medical device.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
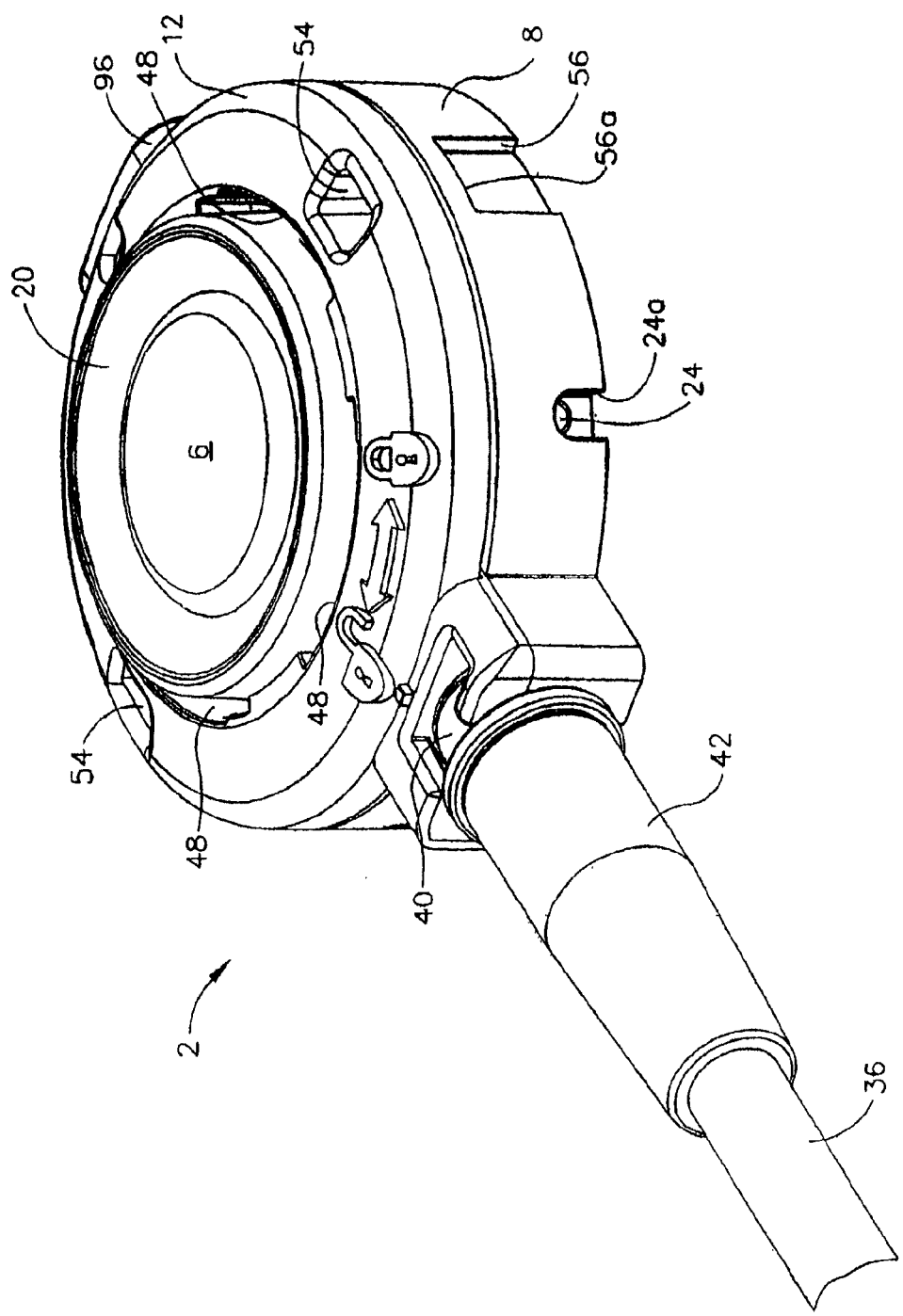
FIG. 1 is a perspective view of an injection port with an attachment mechanism constructed in accordance with the present invention.

Reference will now be made in detail to the present preferred embodiment of the invention, an example of which is illustrated in the accompanying drawings.

DETAILED DESCRIPTION

In the following description, like reference characters designate like or corresponding parts throughout the several views. Also, in the following description, it is to be understood that terms such as front, back, inside, outside, and the like are words of convenience and are not to be construed as limiting terms. Terminology used in this patent is not meant to be limiting insofar as devices described herein, or portions thereof, may be attached or utilized in other orientations. Referring in more detail to the drawings, an embodiment of the invention will now be described.

Referring to FIGS. 1-5, there is shown an implantable medical device, more specifically an injection port, generally indicated at 2, which embodies an attachment mechanism constructed in accordance with the present invention. Although the attachment mechanism is illustrated in the figures as being embodied with injection port 2, the attachment mechanism may be used with any implantable medical device for which it is suited, including by way of example only pace makers, vascular access ports, injection ports (such as used with gastric bands) and gastric pacing devices.

Injection port 2 includes septum retainer 4, septum 6 and port body 8. Injection port 2, with the integrally constructed attachment mechanism, also includes one or more fasteners 10, actuator 12 and a plurality of link members 14.

Figure 4:
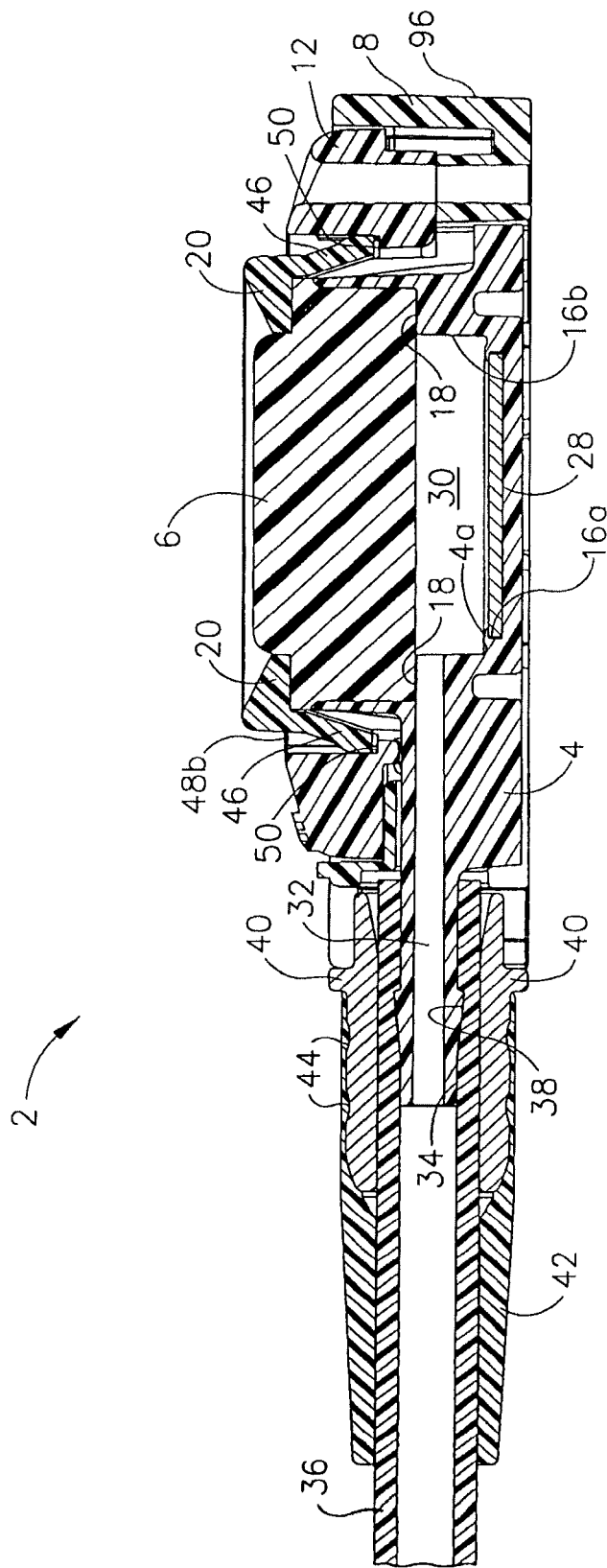
FIG. 4 is a cross sectional view of the injection port of FIG. 1 taken along line 4-4 of FIG. 3.

As seen in FIG. 4, septum 6, which may be made of any biocompatible material such as silicone, is disposed partially within internal cavity 16 of septum retainer 4, adjacent annular flat 18. Septum retainer 4, port body 8, and actuator 12 may be made of any suitable biocompatible material having sufficient stiffness and strength, such as polyetheretherketon (known as PEEK). Fasteners 10 and link members 14 may be made of any suitable biocompatible material, such as stainless steel.

Port body 8 includes annular rim 20, which engages the upper surface of septum 6 about an annular portion. Port body 8 is retained to septum retainer 4 by a plurality of pins 22 which are disposed through respective holes 24 formed in recesses 24a in port body 8 and which extend inwardly into respective recesses 26 formed about the bottom periphery of septum retainer 4. Pins 22 may be made of any suitable biocompatible material, such as stainless steel.

The uncompressed height of septum 6 is approximately 5 mm around the outer diameter and the uncompressed diameter is approximately 18 mm. The exposed diameter for access to reservoir 20 is approximately 14 mm. The distance between the lower surface of annular rim 20 and annular flat 18 is approximately 4 mm, such that septum 6 is compressed approximately 20% to be adequately self healing to maintain a fluid tight system under pressure and still allow a low profile.

Figure 28:
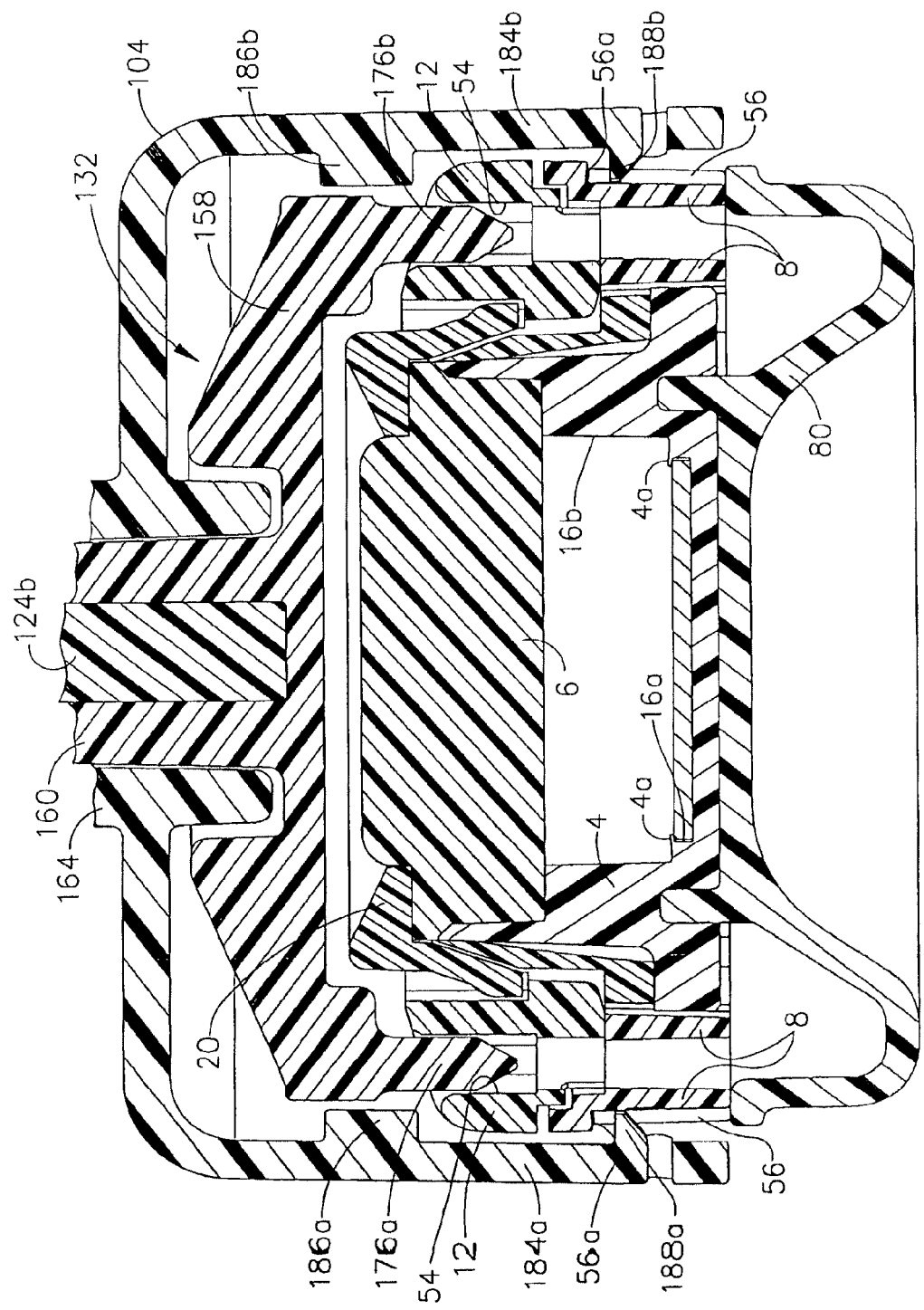
FIG. 28 is an enlarged, cross sectional view of the injection port of FIG. 1 retained by the locator of the applier of FIG. 20.
Figure 29:
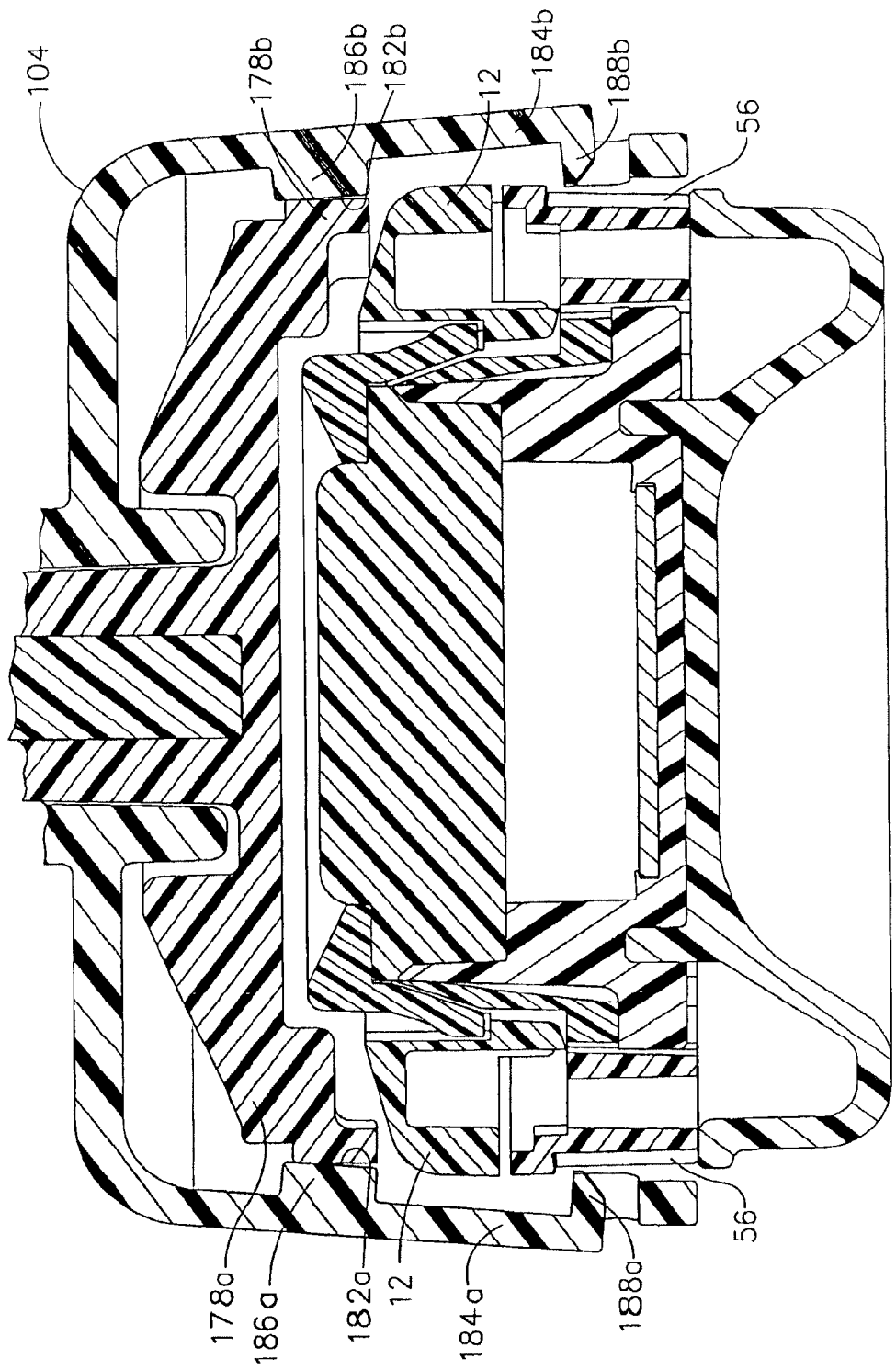
FIG. 29 is an enlarged, cross-sectional view of the injection port of FIG. 1 disposed in the locator of the applier of FIG. 20 after the applier has been actuated to rotate the applier actuator to the deployed position.

Plate 28 is disposed in recess 16a formed in the bottom of septum retainer 4, underlying septum 6 and fluid chamber or reservoir 30. As seen in FIG. 4, plate 28 does not contact sidewall 16b. In the embodiment depicted, plate 28 is metallic, such as stainless steel. When a needle is inserted through septum 6 to introduce or withdraw fluid from fluid chamber 30, such as in order to adjust the size of an adjustable gastric band, metallic plate 28 will protect septum retainer 4 from puncture and provide tactile feedback to the surgeon through the needle indicating that the needle has bottomed in reservoir 30. Plate 28 may be secured to septum retainer 4 in any suitable manner. In the embodiment depicted, plate 28 is held in place by retaining lip 4a extending over the periphery of plate 28 as best seen in FIGS. 4, 28 and 29. Initially, retaining lip 4a extends upwardly as an annular lip, providing clearance for insertion of plate 28 into the recess at the bottom of septum retainer 4, and retaining lip 4a is then rolled or otherwise deformed to overlie at least a portion of the periphery of plate 28 thereby retaining plate 28. In the embodiment depicted the diameter of recess 16a is smaller than the diameter of sidewall 16b, providing room to form the annular lip and to deform it into retaining lip 4a. Plate 28 could be insert molded, with retaining lip 4a molded as illustrated.

Septum retainer 4 includes passageway 32, in fluid communication with fluid chamber 30, which is defined by fitting 34 extending from the periphery adjacent the bottom of retainer 4. Tube 36, which in the embodiment depicted, leads to an adjustable gastric band (not shown), is connected to fitting 34, being compressingly urged against annular rib 38 by connector 40, which is disposed about tube 36 and secured to port body 8 as described below. Sleeve 42 is disposed about tube 36, secured to connector 40 by annular ribs 44. Sleeve 42 relieves strain on tube 36, preventing tube 36 from kinking when loaded laterally.

Figure 5:
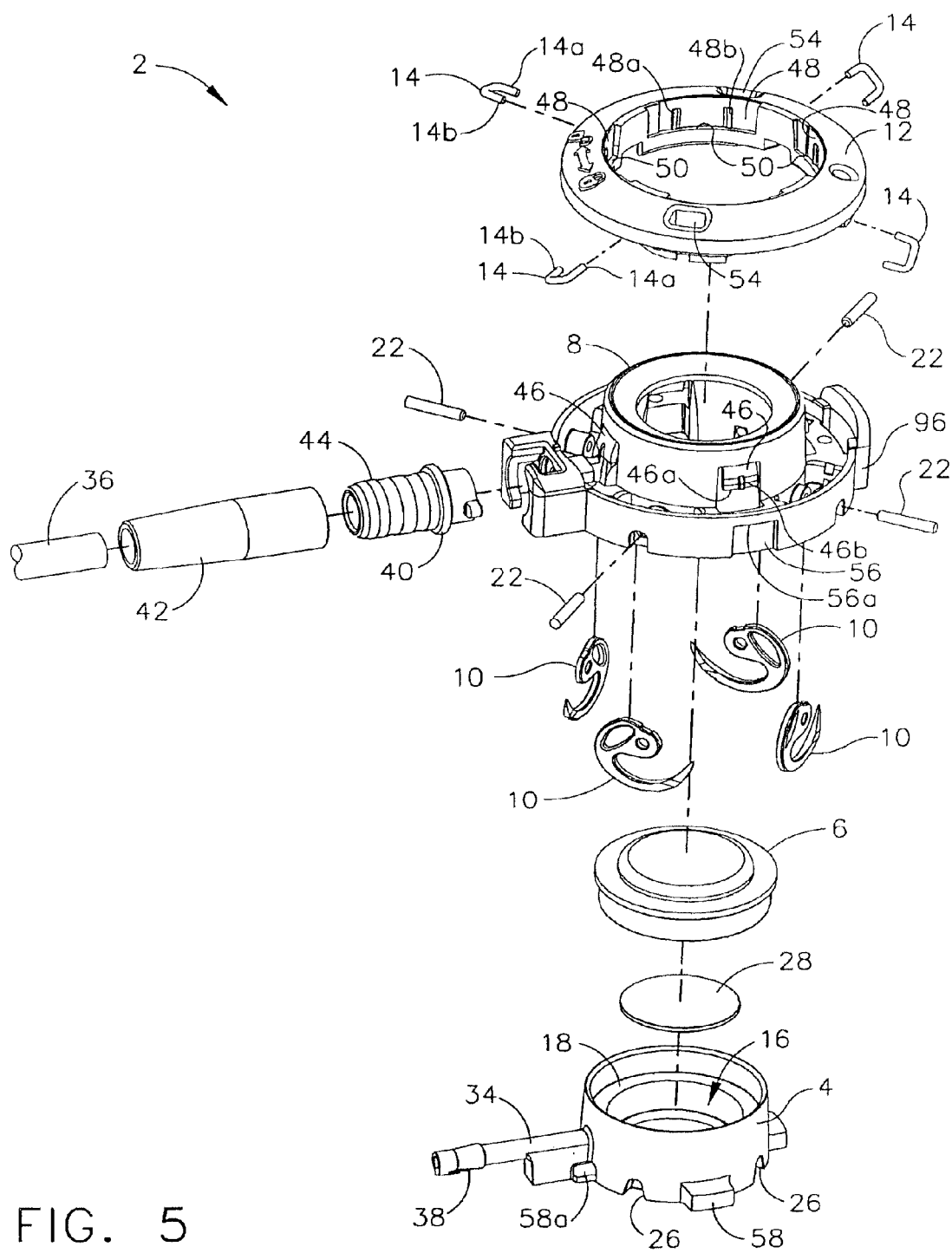
FIG. 5 is an exploded perspective view of the injection port of FIG. 1.

Actuator 12 is secured to port body 8. Although in the embodiment depicted actuator 12 is illustrated as an annular ring rotatably supported by port body 8, actuator 12 may be any suitable configuration and supported in any suitable manner to permit actuator 12 to function to move fasteners 10 between and including deployed and undeployed positions. As seen in FIG. 5, port body 8 includes a plurality of downwardly and outwardly extending tabs 46. In the embodiment depicted, there are four equally spaced tabs 46. Actuator 12 includes an equal number of corresponding recesses 48, each having arcuate bottom 50. To assemble actuator 12 to port body 8, recesses 48 are aligned with tabs 46, and pushed down, temporarily deflecting tabs 46 inwardly until tabs 46 reach recesses 48 and move outwardly to dispose lower edges 46a in recesses 48 such that actuator is retained thereby. The lengths of tabs 46 and depth of recesses 48 allow some axial end play between actuator 12 and port body 8, as will be described below.

Actuator 12 may rotate generally about the central axis of port body 8. In the embodiment depicted, actuator 12 may rotate through an angle of about 40 degrees, although any suitable angle may be used. In the embodiment depicted, when actuator 12 is rotated in the deploying direction, causing fasteners 10 to move to the deployed position, rotation of actuator 12 beyond the fully deployed position is limited by end 48c contacting tab 46.

A detent system is formed by a pair of spaced apart raised detent ribs 48a, 48b extending inwardly from the wall of each recess 48, and a corresponding raised rib 46b extending outwardly from tab 46. The detent system assists in preventing actuator 12 from rotation and fasteners 10 from moving out of fully retracted or fully extended fired states under vibration or incidental loads, as described below.

Actuator 12 includes a plurality of spaced apart openings or slots 54, which may be engaged by any suitable instrument to transmit the necessary torque to actuator 12 to extend fasteners 10 to the actuated position. Slots 54 are configured to be engaged by commercially available instruments, rectangular in the embodiment depicted, or by the dedicated applier described below. Port body 8 includes a plurality of recesses 56 disposed about its lower periphery which are configured to cooperate with the dedicated applier as described below.

Figure 6:
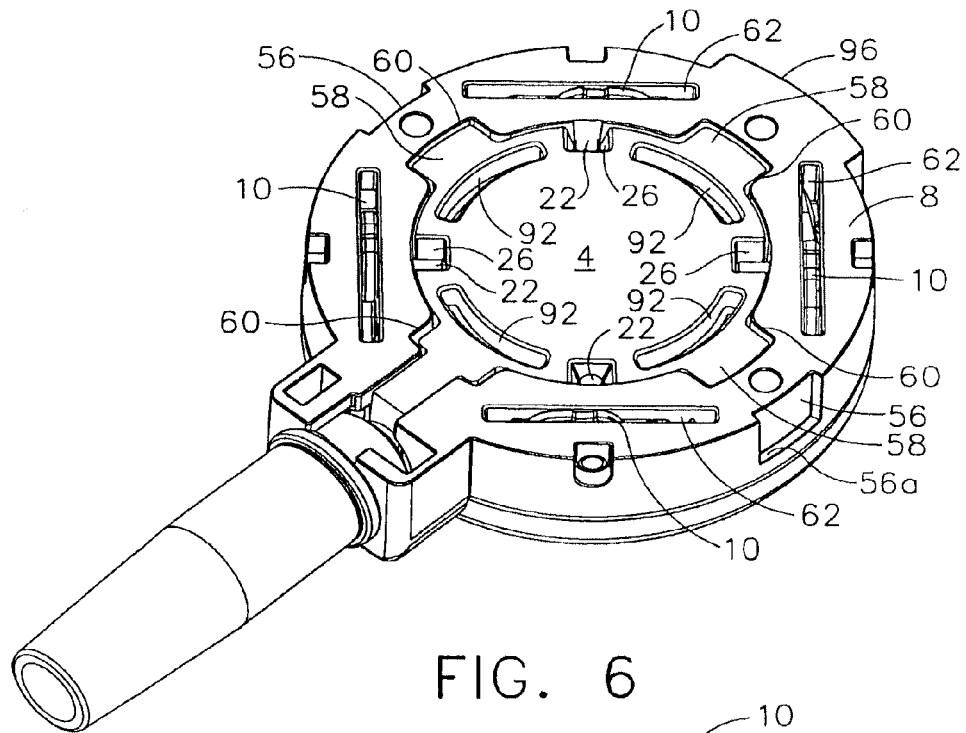
FIG. 6 is perspective view of the bottom of the injection port of FIG. 1, showing the attachment mechanism in the retracted position.
Figure 7:
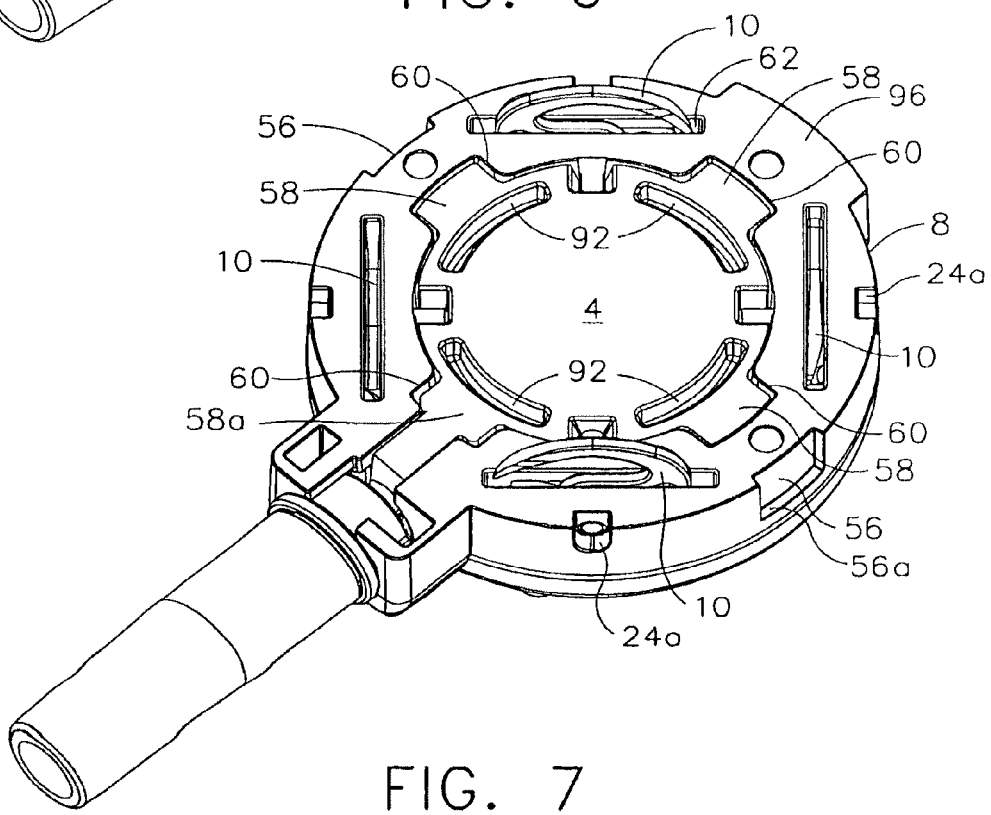
FIG. 7 is a perspective view of the bottom of the injection port of FIG. 1, similar to FIG. 6, showing the attachment mechanism in the extended/fired position.

Referring also to FIGS. 6 and 7, septum retainer 4 includes a plurality of locating tabs 58 extending outwardly from adjacent the bottom periphery of septum retainer 4. Locating tab 58a may be integral with fitting 34. Tabs 58 and 58a are located in respective complementarily shaped recesses 60 formed in the inner surface of port body 8, aligning septum retainer 4 properly with port body 8.

FIG. 6 illustrates fasteners 10 in the retracted position. As can be seen, fasteners 10 are disposed in respective recesses or slots 60 formed in port body 8. FIG. 7 illustrates fasteners 10 in the extended, or fired, position, extending from slots 60. Rotation of actuator 12 moves fasteners 10 from the retracted position to the extended position.

Figure 8:
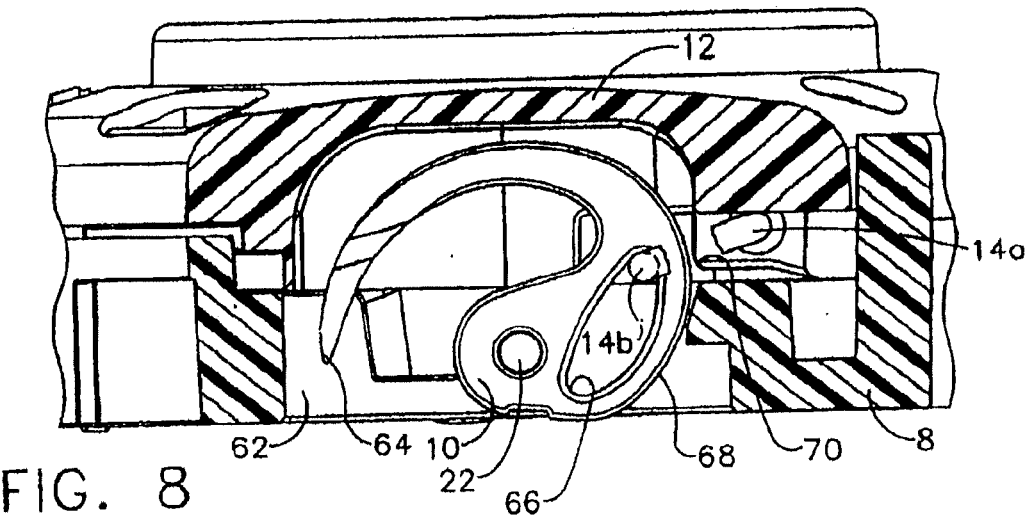
FIG. 8 is a side cutaway view in partial cross-section illustrating a fastener of the attachment mechanism in the retracted position.
Figure 14:
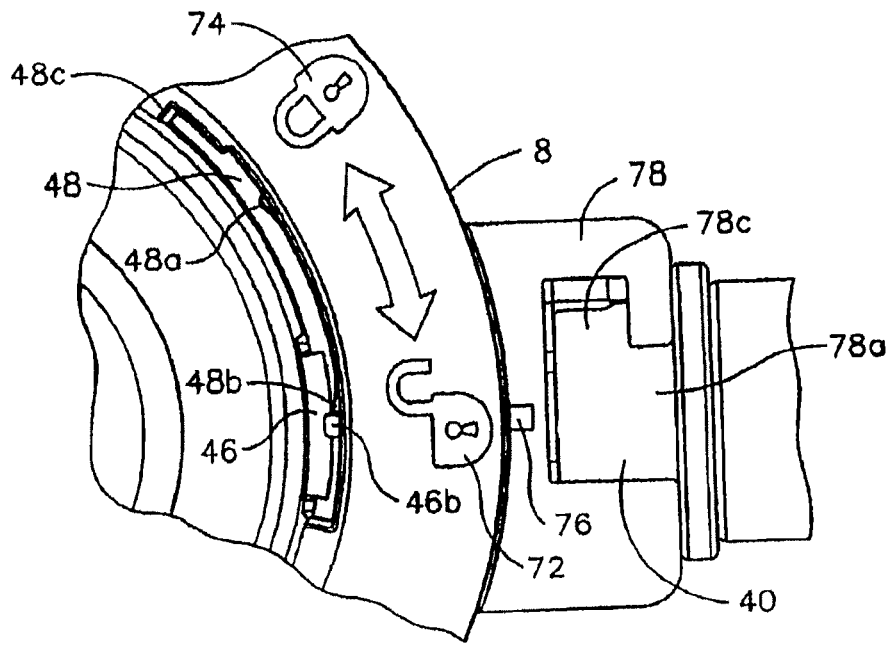
FIG. 14 is an enlarged, fragmentary top view of the visual position indicator and actuator ring detent system of the attachment mechanism of FIG. 1, in the retracted position.

FIGS. 8-11 are a series of figures illustrating the operation of actuator 12 and one of the plurality of fasteners 10, it being understood that the operation on one of fasteners 10 may be the same as for all fasteners 10, which may, in one embodiment, be moved from a deployed position to an undeployed position simultaneously. FIG. 8 illustrates fastener 10 in a fully retracted state, the undeployed position, disposed completely within slot 62 such that sharp tip 64 is not exposed. This prevents tip 64 from accidentally sticking the surgeon or penetrating any object. Actuator 12 is illustrated rotated counter clockwise as far as permitted by recesses 48 and tabs 46. In this position, ribs 46b are disposed clockwise of ribs 48b, as seen in FIG. 14. First ends 14a of link members 14 are rotatably carried by actuator 12, spaced apart at positions corresponding to the positions of fasteners 10. Second ends 14b are disposed within openings 66 of fasteners 10.

To actuate the attachment mechanism, integral actuator 12 is rotated in a deploying direction, which in one embodiment as depicted is clockwise (any suitable direction configured to actuate the attachment mechanism may be used), and rib 46b passes rib 48b, which may produce an audible signal in addition to a tactile signal to the surgeon. Second end 14b of link member 14 is free to move within slot 66 during actuation, as the force that rotates fastener 10 into the extended position is transmitted to fastener 10 through the interaction between cam surface 68 of fastener 10 and actuating cam surface 70 of actuator 12. As actuator 12 rotates clockwise, actuating cam surface 70 engages and pushes against cam surface 68, rotating fastener 10 about pivot pin 22. The majority of the force from actuating cam surface 70 acts tangentially on cam surface 68, off center relative to pivot pin 22, causing fastener 10 to rotate. During actuation, end 14b of link member 14 remains free to move within slot 66, applying no driving force to rotate fastener 10.

Figure 9:
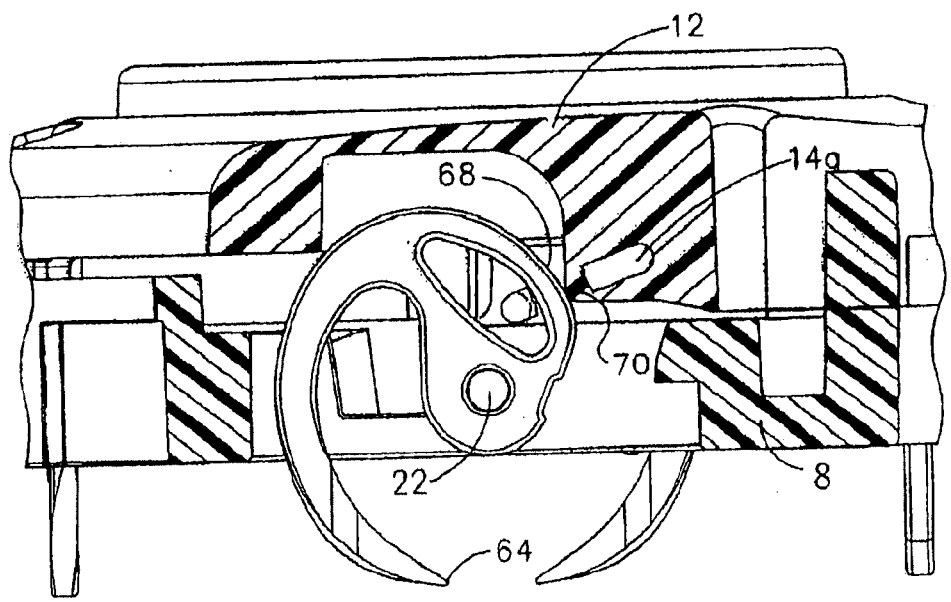
FIG. 9 is a side cutaway view in partial cross-section similar to FIG. 8 illustrating a fastener of the attachment mechanism that is being advanced by the actuator ring toward the extended/fired position.

In FIG. 9, fastener 10 is rotated about half way though its range of rotation, about 90 degrees as a result of the clockwise rotation of actuator 12. As actuator 12 is rotated clockwise, the force between actuator cam surface 70 and cam surface 68 causes actuator 12 to move upward slightly as allowed by the tolerancing of the components. As actuator 12 is rotated further clockwise from the position shown in FIG. 9, actuator cam surface 70 continues to engage and push against cam surface 68, rotating fastener 10 further counterclockwise.

Figure 10:
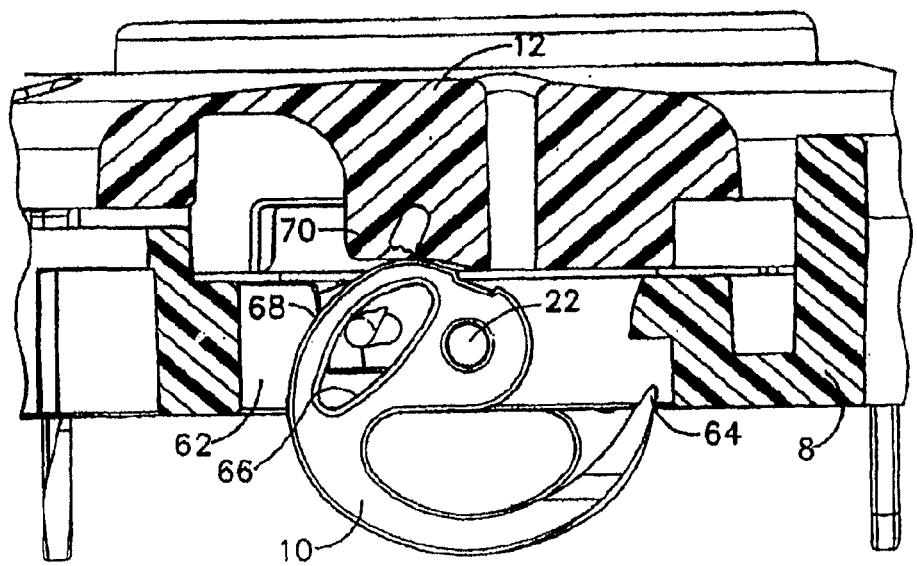
FIG. 10 is a side cutaway view in partial cross-section similar to FIG. 8 illustrating a fastener of the attachment mechanism in the extended/fired position.
Figure 15:
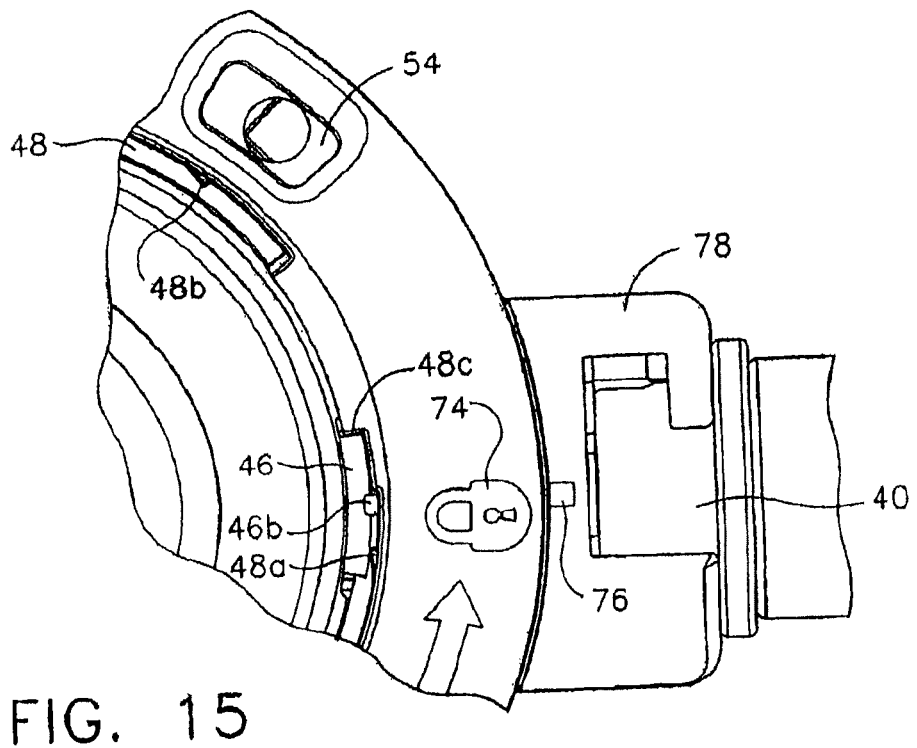
FIG. 15 is an enlarged, fragmentary top view of the visual position indicator and actuator ring detent system of the attachment mechanism of FIG. 1 in the extended/fired position.

In FIG. 10, actuator 12 is rotated clockwise to its fullest extent, with rib 46b having been urged past detent rib 48a (see FIG. 15). In this position, fastener 10 has rotated to its fullest extent, almost 180 degrees in the embodiment illustrated, with tip 64 disposed within recess 62. In this position, actuator cam surface 70 is over center, and actuator 12 is resistant to being back driven by an undeploying force imparted to fastener 10 as cam surface 68 acts against actuator cam surface 70 in a direction that tends to push actuator 12 up instead of rotating actuator 12. The distal end portion of fastener 10 is configured essentially as a beam, depicted as having a generally rectangular cross section along its length, tapering to sharp tip 64. With fastener 10 extending approximately 180 degrees in the fully extended state, the deployed position, forces which might act on fasteners 10 tend to act through the pivot axis defined by pivot pin 22, instead of rotating fasteners 10. It is noted that although pin 22 is illustrated as being a separate piece from fastener 10, the two may be integral or even of unitary construction.

If it is desirable to retract fasteners 10, such as to remove or reposition the implanted device, actuator 12 may be rotated in an undeploying direction, counterclockwise in one embodiment depicted. Starting with the position of actuator 12 shown in FIG. 10, actuator 12 may be rotated counterclockwise, with actuator cam surface 70 sliding against cam surface 68, without rotating fastener 10. In the embodiment depicted, continued counterclockwise rotation of actuator 12 moves cam surface 70 out of contact with cam surface 68, with no substantial rotating force being exerted on fastener 10 until second end 14b of link member reaches a location in slot 66, such as at one end of slot 66, at which link member 14 begins pulling against slot 66 causing fastener 10 to rotate and begin to retract.

Figure 11:
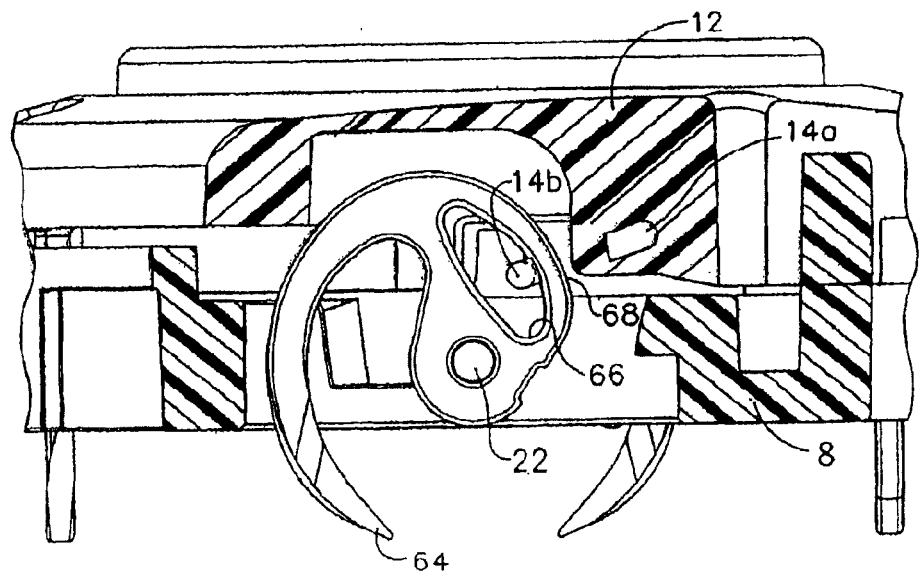
FIG. 11 is a side cutaway view in partial cross-section similar to FIG. 8 illustrating a fastener of the attachment mechanism that is being advanced by the actuator ring toward the retracted position.

As seen in FIG. 11, actuator 12 has been advanced counterclockwise compared to the position shown in FIG. 10, and fastener 10 is rotated approximately halfway through its range. As can be seen by comparing FIG. 9 to FIG. 11, actuator 12 is in different positions with fastener 10 in the same position, in dependence upon whether the attachment mechanism is being actuated or deactuated (retracted). This results from the lost motion that results when link member 14 is pulling on slot 66 in comparison to actuator cam surface 70 pushing directly on cam surface 68. To retract fasteners 10 fully, actuator 12 is rotated until detent rib 46b snaps past detent rib 48b.

Referring to FIG. 8, when fasteners 10 reach the fully undeployed position tip 64 may be disposed fully in slot or recess 62. Further undeploying rotation of actuator 12 is prevented by link member 14 which is prevented from further movement by fastener 10.

Figure 2:
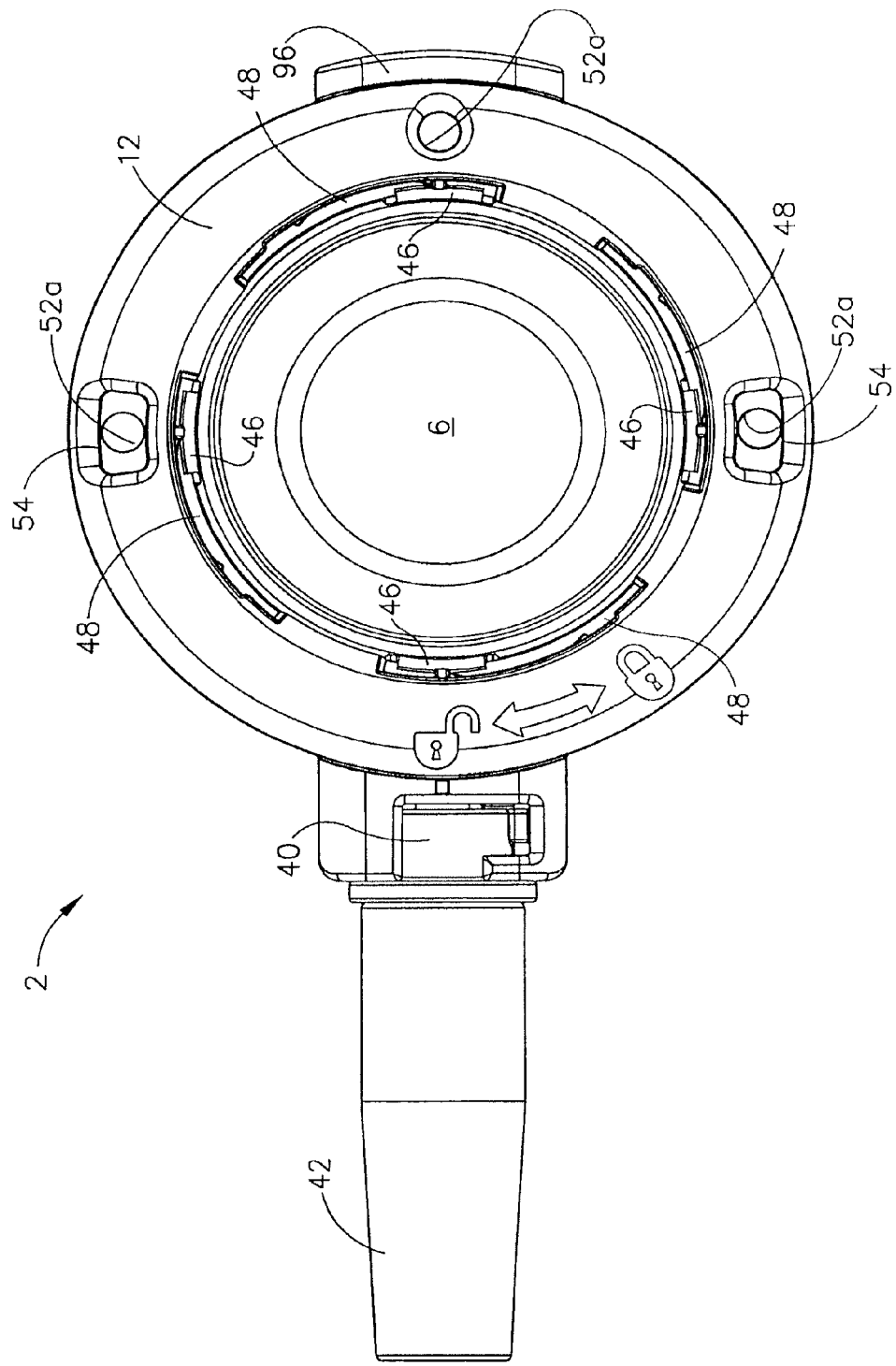
FIG. 2 is a top view of the injection port of FIG. 1.
Figure 3:
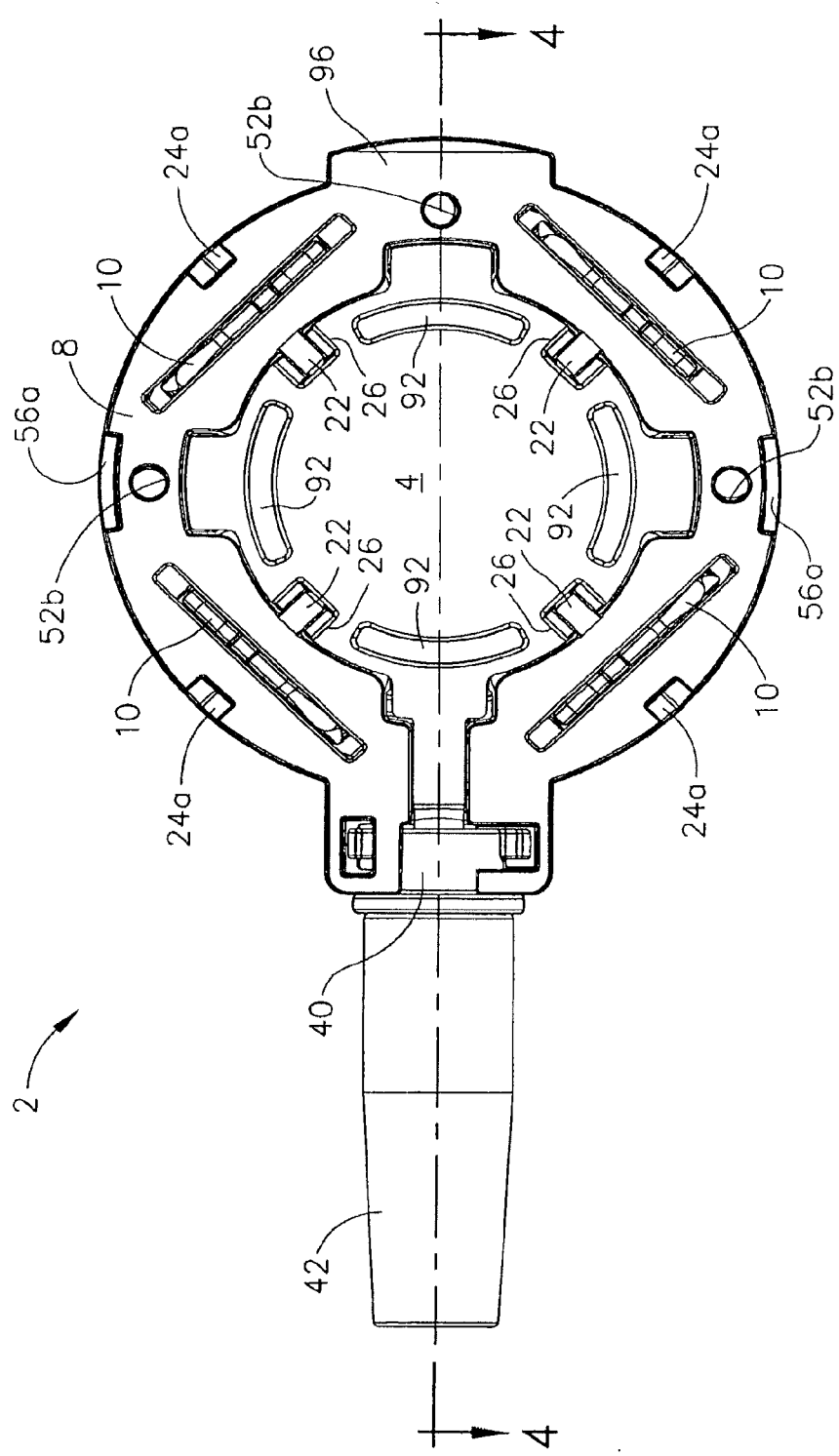
FIG. 3 is a bottom view of the injection port of FIG. 1.

Referring to FIGS. 2 and 3, actuator 12 includes openings 52a formed therethrough, which align with corresponding openings 52b formed in port body 8 when actuator is in the undeployed position. Openings 52a and 52b may be used by the surgeon to suture injection port 2 if the integral attachment mechanism is not used.

Figure 12:
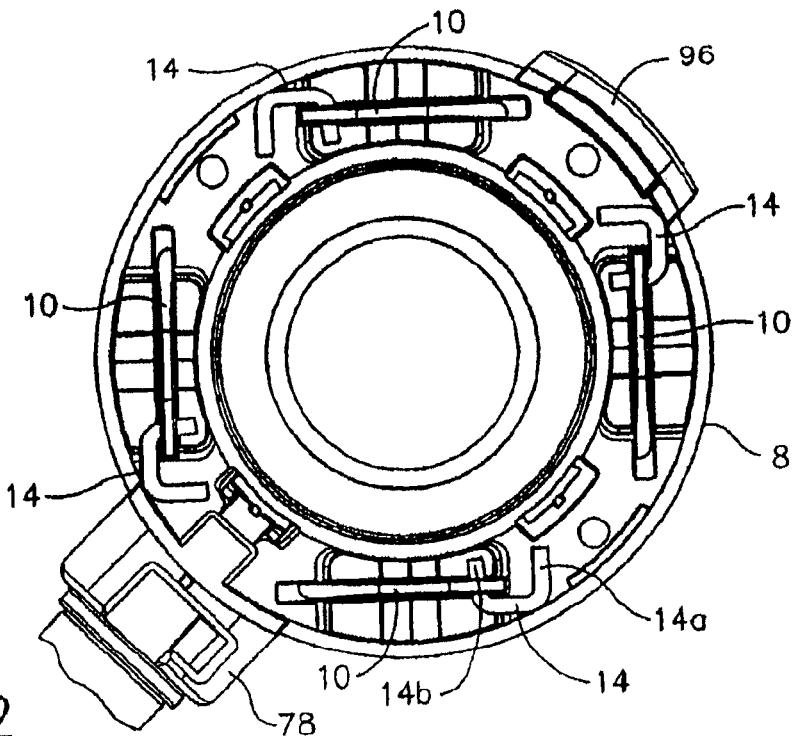
FIG. 12 is a top view of the injection port of FIG. 1, with the actuator ring omitted to illustrate the positions of the links when the fasteners are in the retracted position.
Figure 13:
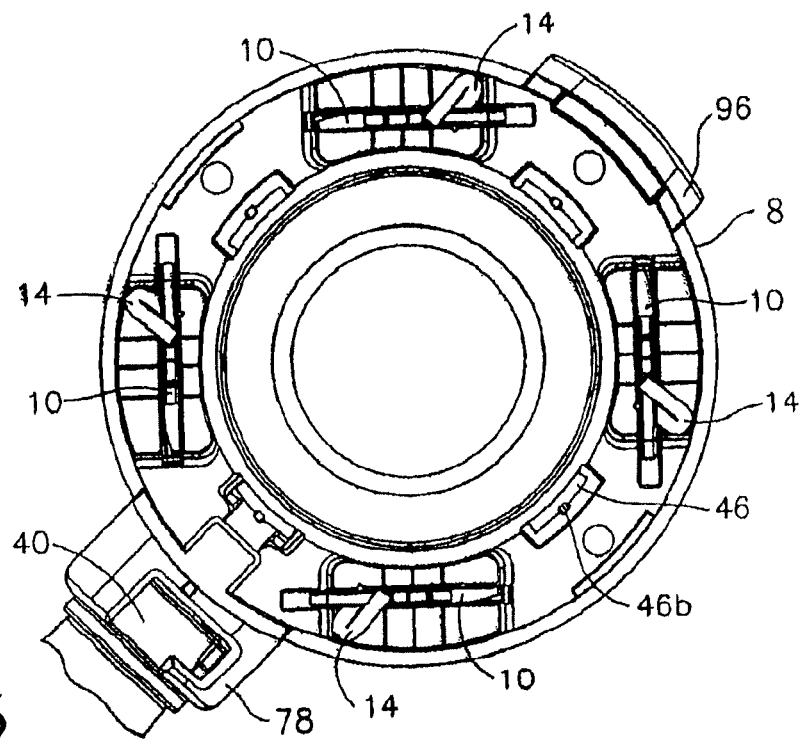
FIG. 13 is a top view of the injection port of FIG. 1, with the actuator ring omitted to illustrate the positions of the links when the fasteners are in the extended/fired position.

Referring to FIGS. 12 and 13, the attachment mechanism is shown without actuator 12. Link members 14 are shown in their actual positions when first ends 14a are supported by actuator 12, in the deployed and in the undeployed states.

Referring to FIGS. 14 and 15, there is illustrated a top view of the visual position indicator and a portion of the actuator ring detent system of the attachment mechanism as embodied in injection port 2. In FIG. 14, the attachment mechanism is in the retracted, undeployed state or position. In this position, detent rib 46b is clockwise of detent rib 48b, and thus in the undeployed detent position. In FIG. 15, the attachment mechanism is in the actuated or deployed position. In this position, detent rib 46b is counterclockwise of detent rib 48b, and thus in the deployed detent position.

FIGS. 14 and 15 illustrate a visual indicator of the state of the attachment mechanism. As seen in FIG. 14, indicia may be utilized, such as an unlocked lock icon 72 and a locked lock icon 74 molded integral with actuator ring 12. Any suitable graphic indicator may be used, and may be printed on or otherwise applied in a suitable manner. Port body 8 may include indicator 76 to provide a reference point for the movable indicia. Arrow 78 may be included to indicate the bidirectional motion of actuator 12.

Figure 16:
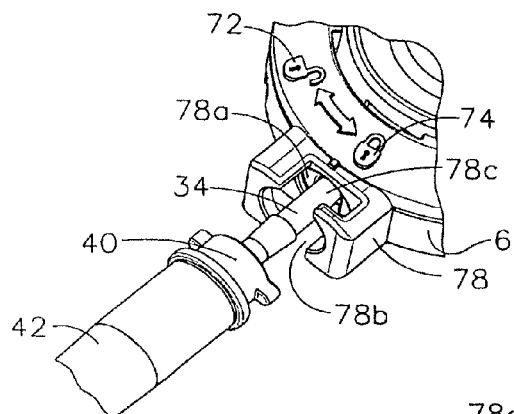
FIG. 16 is an enlarged, fragmentary, exploded perspective view of the fitting and locking connector of the injection port of FIG. 1.
Figure 17:
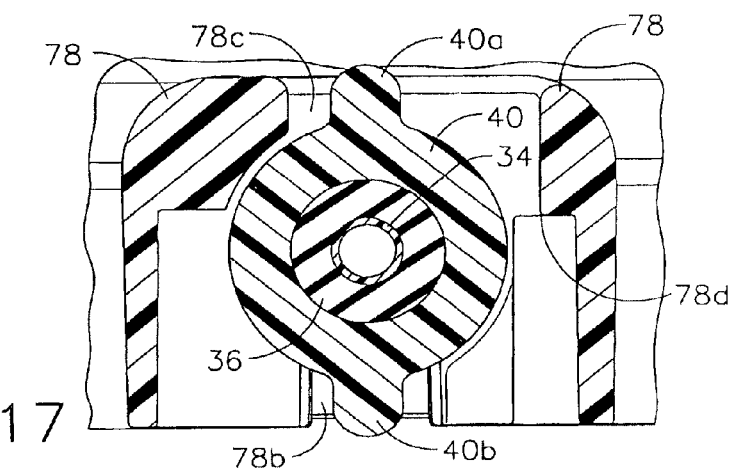
FIG. 17 is an enlarged, fragmentary partial cross-section view of the locking connector assembled to the fitting the septum retainer but not locked in place.
Figure 18:
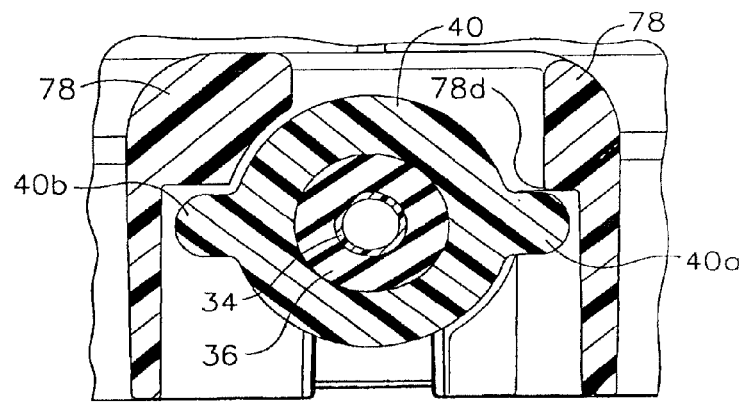
FIG. 18 is an enlarged, fragmentary partial cross-section view similar to FIG. 17 showing the locking connector locked in place.

FIGS. 16-18 illustrate the locking connection between connector 40 and port body 8. FIG. 16 is an exploded perspective view showing fitting 34 partially surrounded by extension 78. FIG. 17 shows extension 78 in cross-section, with connector 40 generally disposed about fitting 34 and tube 36 aligned in circumferential slot 78c of extension 78. Connector 40 includes a pair of tabs 40a, 40b, extending outwardly therefrom. To assemble, connector 40 is guided along tube 36 and fitting 34, with tabs 40a and 40b aligned with openings 78a and 78b of extension 78. With tabs 40a and 40b aligned with circumferential slot 78c, connector 40 is rotated to lock it in place. During rotation, detent edge 78d creates interference opposing the rotation of tab 40a, but is dimensioned to allow tab 40a to be rotated past, to the locked position seen in FIG. 18.

Figure 19:
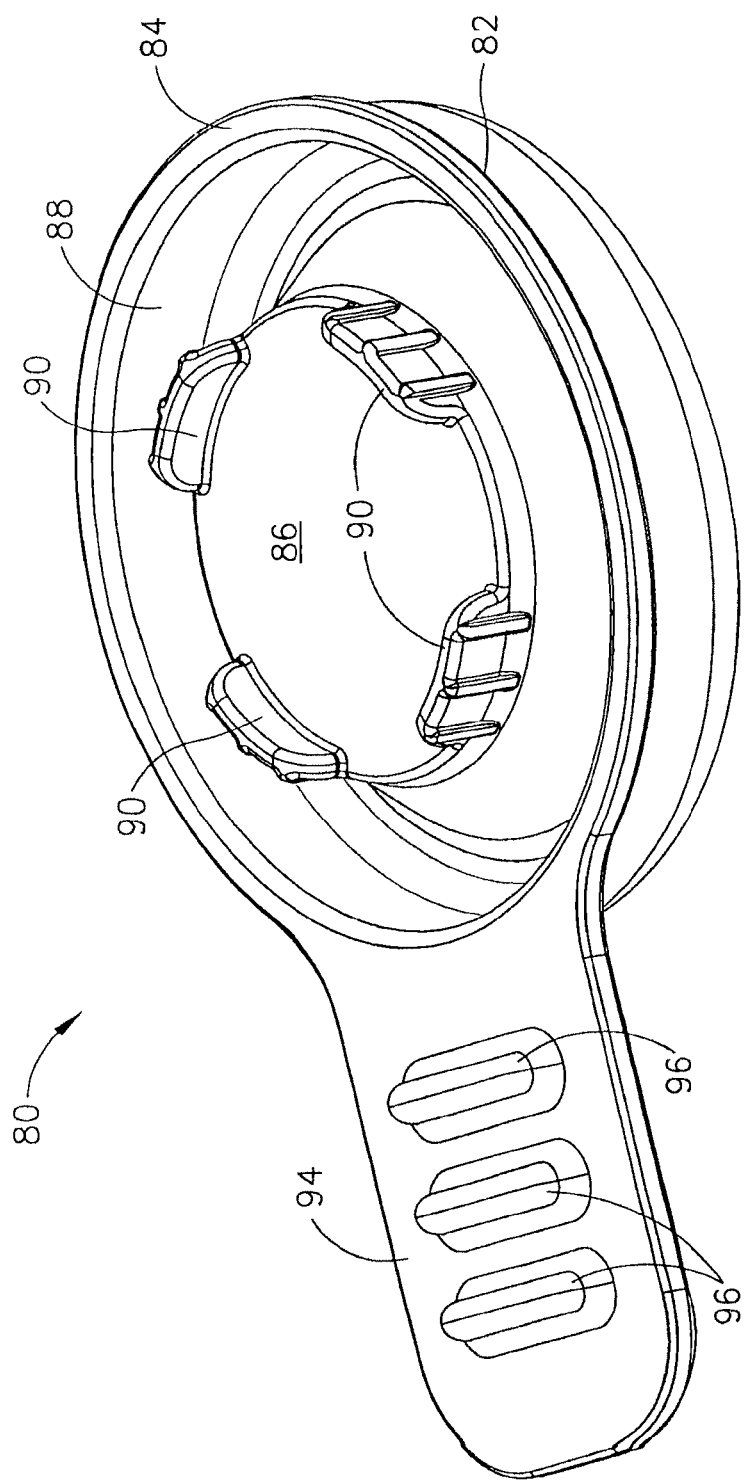
FIG. 19 is an enlarged perspective view of the safety cap.

FIG. 19 illustrates safety cap 80 which may be removably secured to the bottom of injection port 2 to cover fasteners 10 to protect users from accidental exposure to sharp tips 64 while handling injection port 2. Safety cap 80 includes body 82 with annular rim 84 and raised center 86 defining annular recess 88. Safety cap 80 may be oriented and retained to injection port through any suitable configuration. As depicted, body 82 includes a plurality of arcuate retention tabs 90 extending upwardly from raised center 86. Arcuate retention tabs 90 are shaped complementarily to corresponding arcuate slots 92, best seen in FIGS. 3, 6 and 7, and may have ribs as shown. Safety cap 80 is secured to injection port 2 by inserting arcuate retention tabs 90 into arcuate slots 92, which are sized to retain tabs 90. Fasteners 10 are thus aligned with annular recess 88, which is sized to allow fasteners 10 to be extended without contacting safety cap 80. As depicted, since arcuate retention tabs 90 and arcuate slots 92 are respectively the same size and equally spaced, safety cap 80 is not indexed to a particular position, and may be secured to injection port 2 in four different positions. Safety cap 80 includes pull tab 94 with raised a plurality of ribs 96 to provide a better gripping surface. Although pull tab 94 may be oriented in any suitable orientation, in the embodiment, the relative position between pull tab 94 and arcuate retention tabs 90 locates pull tab at 45 degrees to the direction of connector 40. Tabs 90 and slots 92 may be of any suitable shape.

Figure 20:
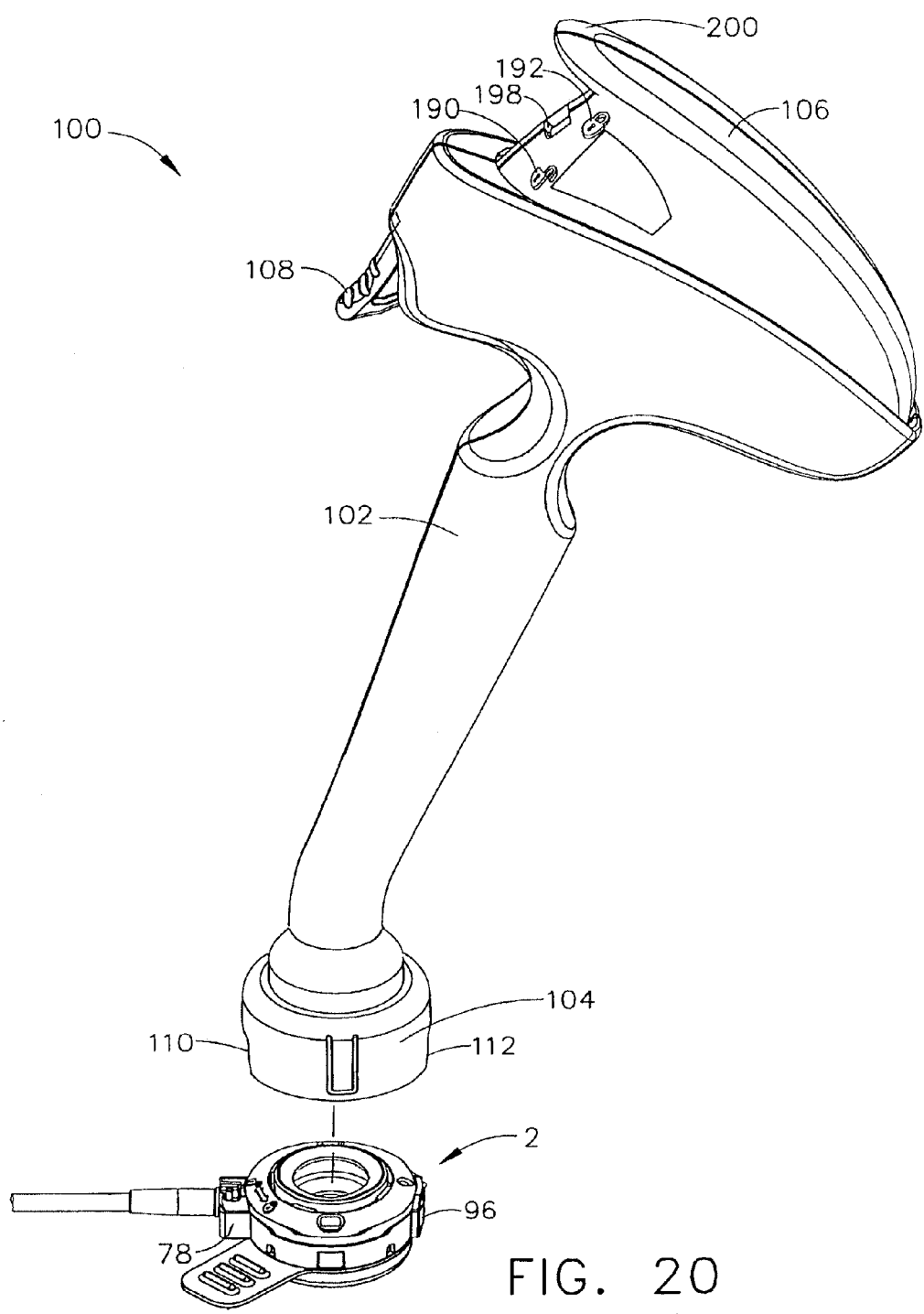
FIG. 20 is a perspective view of an applier constructed to implant the injection port of FIG. 1.

As mentioned previously, the attachment mechanism may be actuated by engaging slots 54 with commercially available instruments or by a dedicated applier. FIG. 20 illustrates applier, generally indicated at 100, which is configured to position, actuate, deactuate, remove or reposition injection port 2. It is noted that the practice of aspects of the present invention as applied to an applier is not limited to the specific applier embodiment depicted herein.

As shown in FIG. 20, applier 100 includes body 102, locator 104, actuator 106 and safety switch 108. As will be described below, injection port 2 may be assembled to locator 104, with extension 78 and tab 96 disposed in alignment slots 110 and 112. Locator 104 is angled relative to body 102, allowing for easier and better visualization of injection port 2 during implantation. In the embodiment depicted, the angle is 20 degrees and the shaft portion of body 102 is 10 cm.

Figure 21:
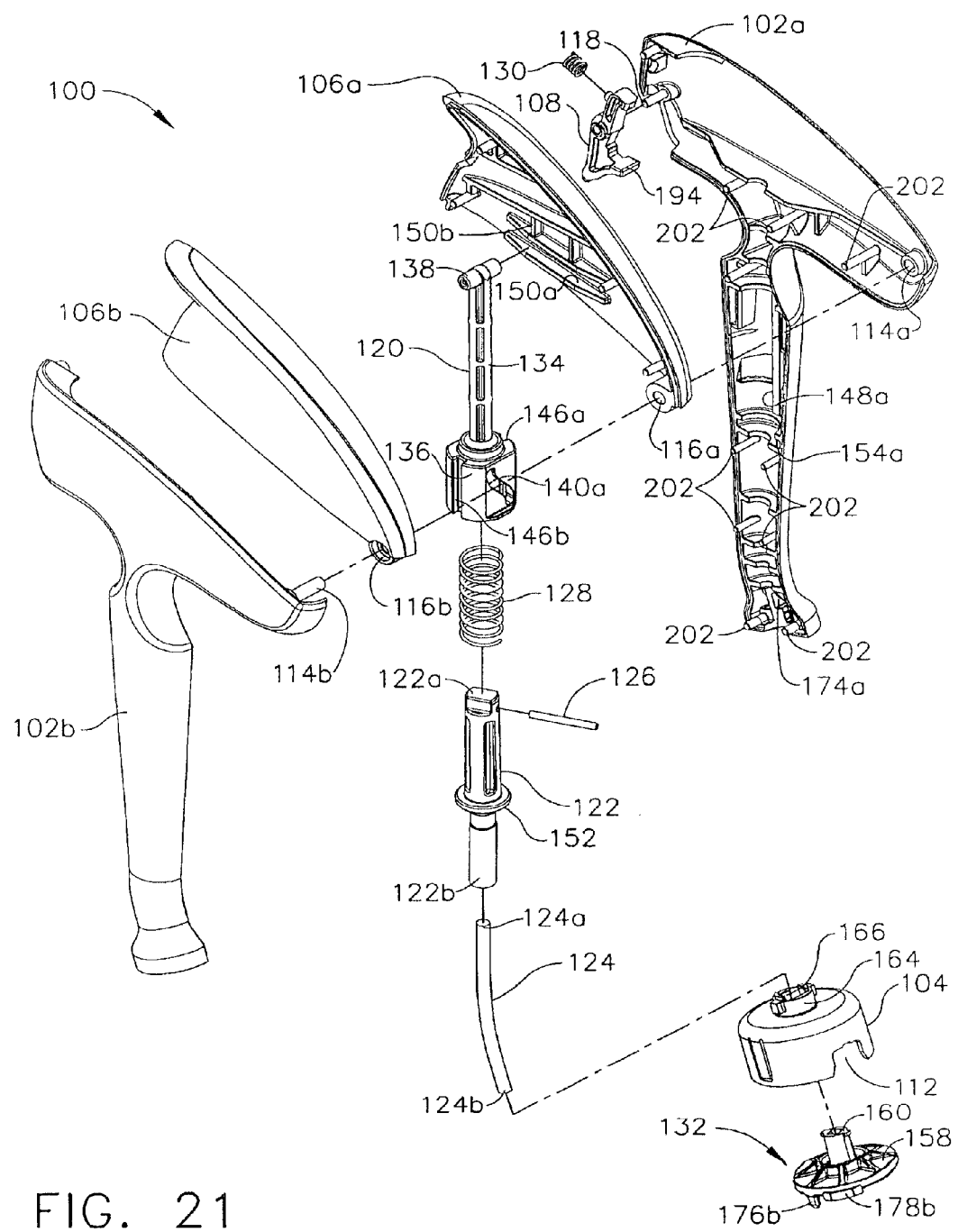
FIG. 21 is a exploded, perspective view of the applier of FIG. 20.

Referring to FIG. 21, body 102 includes first and second halves 102a and 102b assembled to each other to contain the internal components. Except for locating pins 202, pivot pins 114 and ship laps, body halves 102a and 102b are substantially similar to each other. Locating pins 202, illustrated as extending from body half 102a, fit into respective complementarily shaped openings (not illustrated) on body half 102b. The engagement of the plurality of locating pins 202 in the openings is sufficient to hold body halves 102a and 102b together. Pins 202 may alternatively extend from body half 102b with the openings carried by body half 102a. Any suitable configuration may be used to assemble and secure body halves 102a and 102b together.

Actuator 106 includes first and second halves 106a and 106b. Locating pins 204, illustrated as extending from actuator half 106a, fit into respective complementarily shaped openings (not illustrated) on actuator half 106b. Pins 204 may alternatively extend from actuator half 106b with the openings carried by actuator half 106a. Any suitable configuration may be used to assemble and secure actuator halves 106a and 106b together. Body half 102b includes pivot pin 114b which rotatably supports actuator 106 at one end, extending through pivot holes 116a and 116b into opening 114a. Body half 102a includes pivot pin 118b (see FIG. 22) which rotatably supports safety switch 108. Body halves 102a and 102b, locator 104, actuator halves 106a and 106b, and safety switch 108 may be made of any biocompatible material such as polycarbonate.

Referring to FIGS. 21-24, applier 100 includes cam 120, drive shaft 122 with flexible shaft 124, drive shaft pin 126, cam return spring 128, safety biasing spring 130, and actuator 132. Actuator 132 is configured to effect the deployment or undeployment of the attachment mechanism of the medical implant. Cam 120 includes shaft 134 and cam collar 136. The upper end of shaft 134 has a "T" configuration terminating in cross member 138. Cam collar 136 defines a hollow interior and a pair of spaced apart, complementarily shaped cam tracks 140a and 140b formed on opposite sides of cam collar 136. Upper end 122a of drive shaft 122 is disposed partially within the hollow interior defined by cam collar 136, captured therein by drive shaft pin 126. Drive shaft pin 126 is sized such that each end is located within a respective cam track 140a, 140b. The length of the hollow interior allows upper end 122a to reciprocate therein, with cam tracks 140a and 140b imparting rotation to drive shaft 122 through drive shaft pin 126 during reciprocation. Cam 120, drive shaft 122 and actuator 132 may be made of any suitable material having sufficient stiffness and strength. In the embodiment depicted, cam 120 and actuator 132 are made of a liquid crystal polymer such as Vectra™ LCP, and drive shaft 122 is made of a PPE+PS such as Noryl™. Drive shaft pin 126 and cam return spring 128 may be made of any suitable material, such as stainless steel.

Cam 120 is retained between body portions 102a and 102b, and in one embodiment, such as that depicted can reciprocate. Cam collar 136 has spaced apart, generally flat outer surfaces 142a and 142b tracks through which 140a and 140b are formed. These surfaces 140a and 140b are disposed between guide walls 144a and 144b formed in body portions 102a and 102b. Cam collar 136 also includes oppositely facing channels 146a and 146b (see FIG. 23), which are guided for axial reciprocation by guides 148a and 148b (not illustrated) formed in body portions 102a and 102b, respectively. The upper end of shaft 134 and cross member 138 are disposed sandwiched between actuator halves 106a and 106b. Each actuator half 106a, 106b, includes a cam track 150 defined by a pair of spaced apart walls 150a and 150b extending from the interior surfaces of actuator halves 106a and 106b. Cam track 150 is configured to receive and guide cross member 138 as actuator 106 is rotated about pin 114, forcing cam 120 to advance linearly downwardly into body 102.

Drive shaft 122 includes annular collar 152 which is received in slots 154a and 154b (not illustrated) formed in body halves 102a and 102b, respectively. Slots 154a and 154b rotatably support drive shaft 122. Drive shaft 122 and cam 120 are generally aligned and collinear with each other, defining the axis of the shaft portion of body 102. As cam 120 is advanced downwardly, drive shaft pin 126 follows cam tracks 140a and 140b, causing drive shaft 122 to rotate, thus converting linear motion to rotary motion. Cam return spring 128 provides a nominal return force against cam collar 136.

Flexible shaft 124 is supported by a plurality of ribs 156, formed in each body half 102a, 102b, which support the bend in flexible shaft 124 that permits the rotary motion to be transferred to actuator 132 which is disposed at an angle relative to the shaft of body 102. Flexible shaft 124 may be made of any suitable biocompatible material, such as stainless steel. In an embodiment depicted, flexible shaft 124 has a stranded construction, with a center core having multiple layers of wire wrapped thereabout. Ends 124a and 124b of flexible shaft 124 may be attached to end 122b and actuator 132, respectively, in any suitable manner which sufficiently limits rotational end play to prevent or minimize lost rotational motion. In an embodiment depicted, end 124a was overmolded into end 122b, and end 124b was press fit into actuator 132. Alternatively, end 124a could be press fit into end 122b, and end 124b overmolded into actuator 132, both could be press fit, or both could be overmolded (with a corresponding change to the configuration of locator 104 to allow assembly.

Referring to FIGS. 21-25, actuator 132 includes disc shaped member 158 and shaft 160 extending upwardly therefrom. The upper end of shaft 160 includes a pair of outwardly extending tabs 162a and 162b. Locator 104 includes hub 164 defining bore 166 therethrough. Bore 166 is shaped to receive and rotatably support shaft 160, and includes two outwardly extending arcuate recesses 168a and 168b configured to provide assembly clearance for tabs 162a and 162b, allowing hub 164 to be inserted into bore 166. The lengths of shaft 160 and hub 164 are sized such that tabs 162a and 162b are located above upper surface 164a of hub 164, allowing rotation of actuator 132 while retaining it axially relative to hub 164. Stops 170 and 170b extend upwardly from upper surface 164a, limiting the rotation of actuator 132. Bore 166 defines a central axis of locator 104 about which actuator 132 is rotated. The central axis of locator 104 is disposed at an angle to the axis of the shaft portion of body 102, as previously mentioned.

Hub 164 includes a pair of oppositely extending tabs 172a and 172b which retain port actuator 104 to body 102 and prevent rotation. Body halves 102a and 102b include respective recesses 174a (see FIG. 21) and 174b (not illustrated) shaped complementarily to tabs 172a and 172b.

Figure 26:
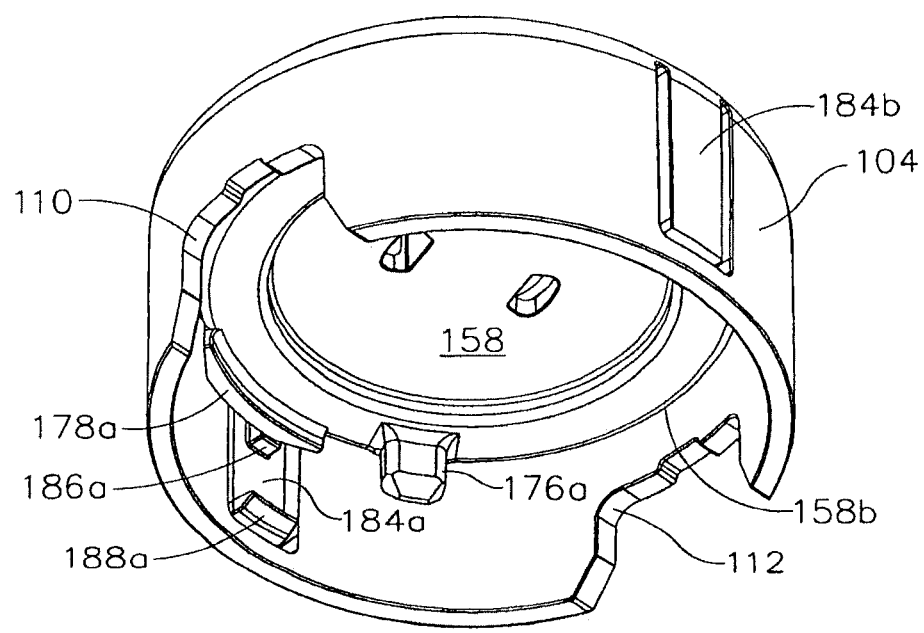
FIG. 26 is an enlarged bottom perspective view of the locator and the port actuator of the applier of FIG. 20.
Figure 27:
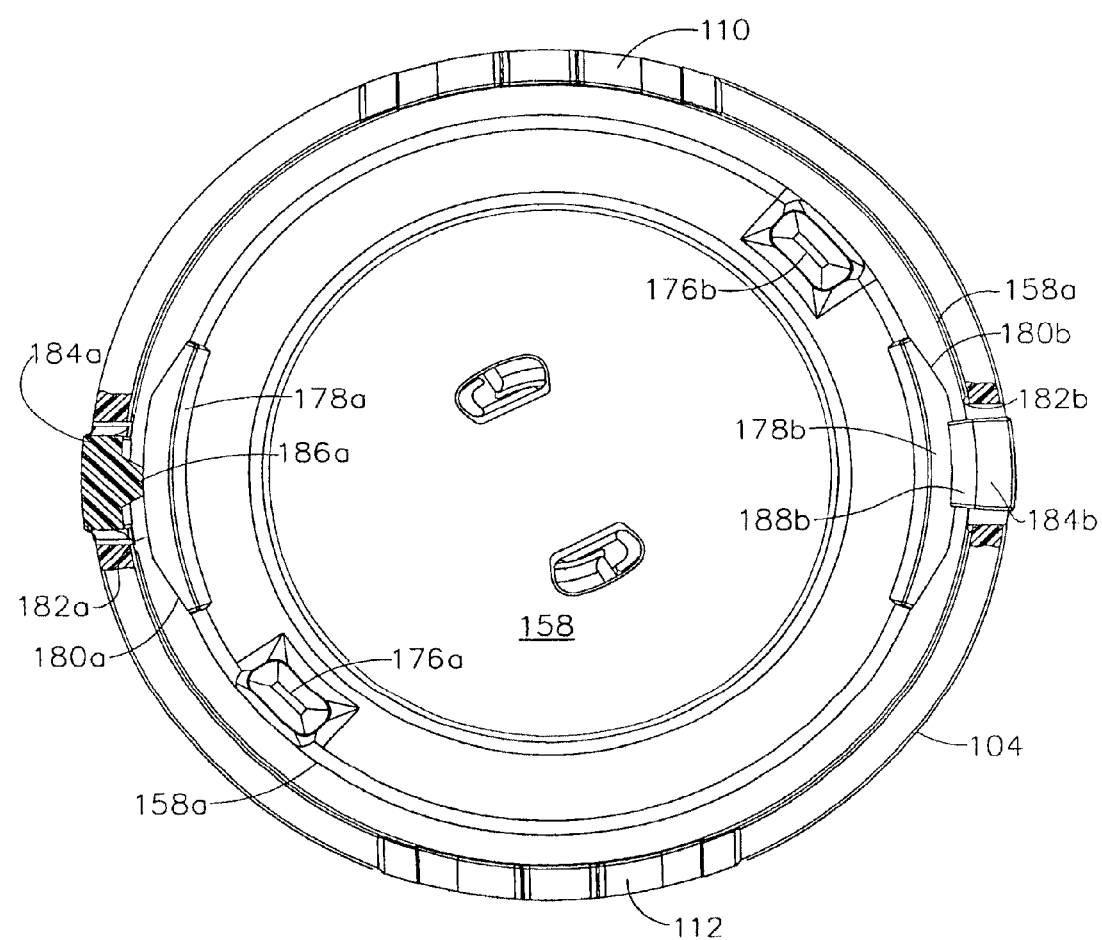
FIG. 27 is a partially cut away end view of the locator of the applier of FIG. 20.

Referring also to FIGS. 26 and 27, disc shaped member 158 of actuator 132 is seen disposed within locator 104. Actuator 132 includes a pair of spaced apart posts 176a and 176b, extending from adjacent periphery 158a of member 158. Posts 176a and 176b are shaped complementarily with openings 54. In the embodiment depicted, the distal ends of posts 176a and 167b are tapered to assist in guiding posts 176a and 176b into openings 54. Any suitable configuration may be utilized to create releasable contact between actuator 132 and actuator 12 capable of actuating actuator 12.

Disc shaped member 158 also includes a pair of spaced apart cams 178a and 178b which extend outwardly and upwardly from periphery 158a of member 158. FIG. 27 illustrates cam 178a at a cross-section taken near the bottom surface of member 158. Cams 178a and 178b include ramps 180a and 180b which start at periphery 158a and lead out to surfaces 182a and 182b, respectively. Each surface 182a, 182b is arcuate, shown in the embodiment depicted as generally having a constant radius.

In the embodiment depicted, locator 104 includes a port engagement portion or port engagement feature comprising a pair of spaced apart cantilever arms 184a and 184b, each having rib 186a and 186b, respectively. For clarity, FIG. 27 illustrates arm 184a in cross-section taken through rib 186a, at the same level as for cam 178a. At their distal ends, arms 184a and 184b include respective inwardly extending flanges 188a and 188b. Flanges 188a and 188b are shaped complementarily to recesses 56 on port body 8, configured to engage ledges 56a that form an applier engagement portion when injection port 2 is retained by locator 104.

In the embodiment depicted, in the non-actuated state, posts 176a and 176b are generally aligned with arms 184a and 184b, respectively, although posts 176a and 176b may be at any position that corresponds to position of the actuating feature of actuator 12, which in the embodiment depicted is openings 54. As actuator 106 is depressed, actuator 132 rotates (counterclockwise in the embodiment depicted when viewed from the bottom), advancing cams 178a and 178b such that ramps 180a and 180b contact ribs 186a and 186b, respectively, deflecting arms 184a and 184b outwardly. When surfaces 182a and 182b engage ribs 186a and 186b, arms 184a and 184b are deflected a distance sufficient to move flanges 188a and 188b to a position where they no longer extend into recesses 56 or contact ledges 56a, thus releasing injection port 2 from locator 104.

FIG. 28 illustrates injection port 2 disposed in and retained by locator 104, with extension housing 78 and tab 96 disposed in slots 110 and 112, respectively (see FIG. 20, not seen in FIG. 28). As depicted, posts 176a and 176b extend into openings 54 of actuator 12, and flanges 188a and 188b extending into recesses 56 proximal ledges 56a. Safety cap 80 is connected to injection port 12 when injection port 12 is inserted into locator 104, covering fasteners 10 (not seen in FIG. 28).

Figure 22:
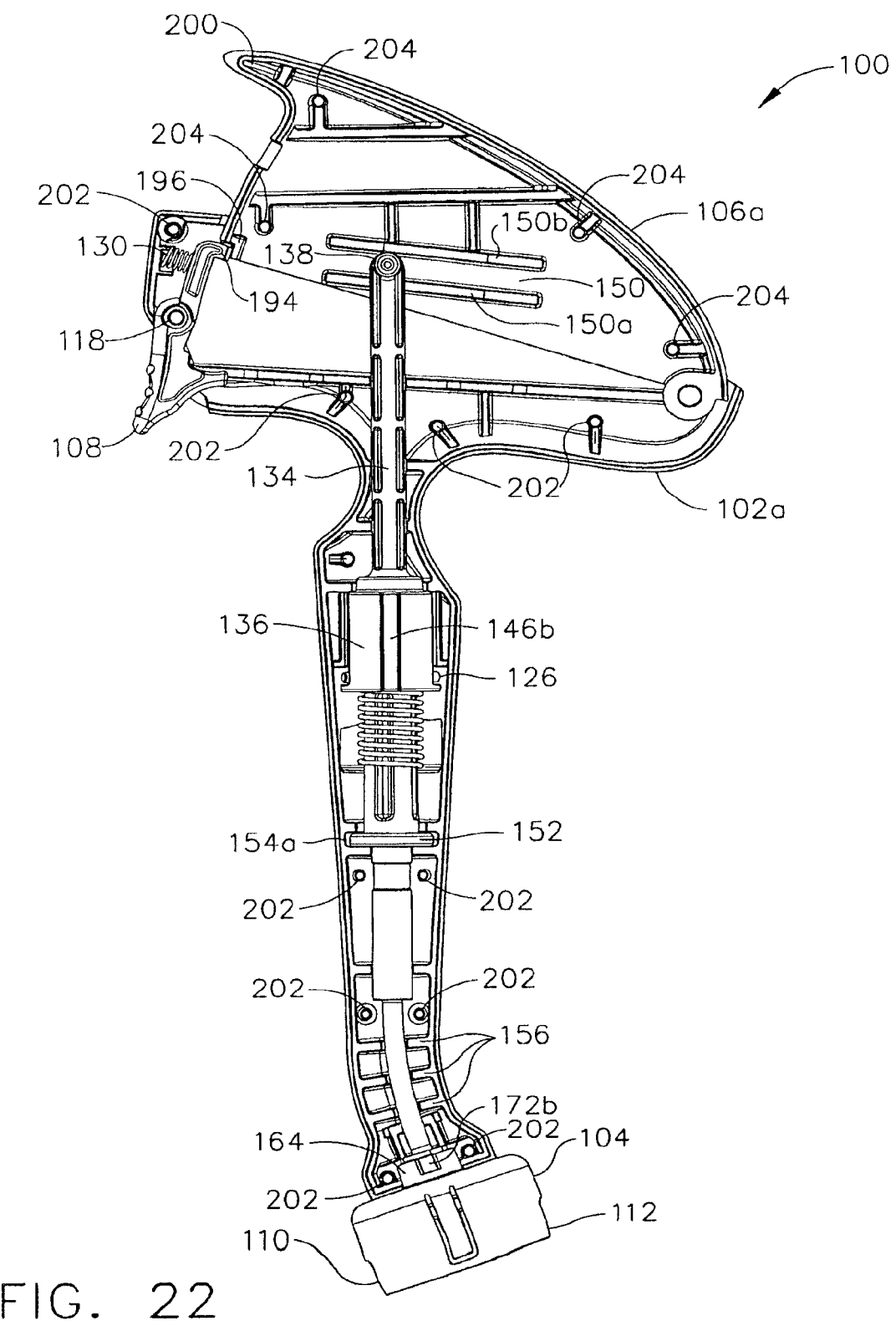
FIG. 22 is a side view of the applier of FIG. 20 with one of the two body halves showing the internal components in the unapplied, non-actuated position.
Figure 23:
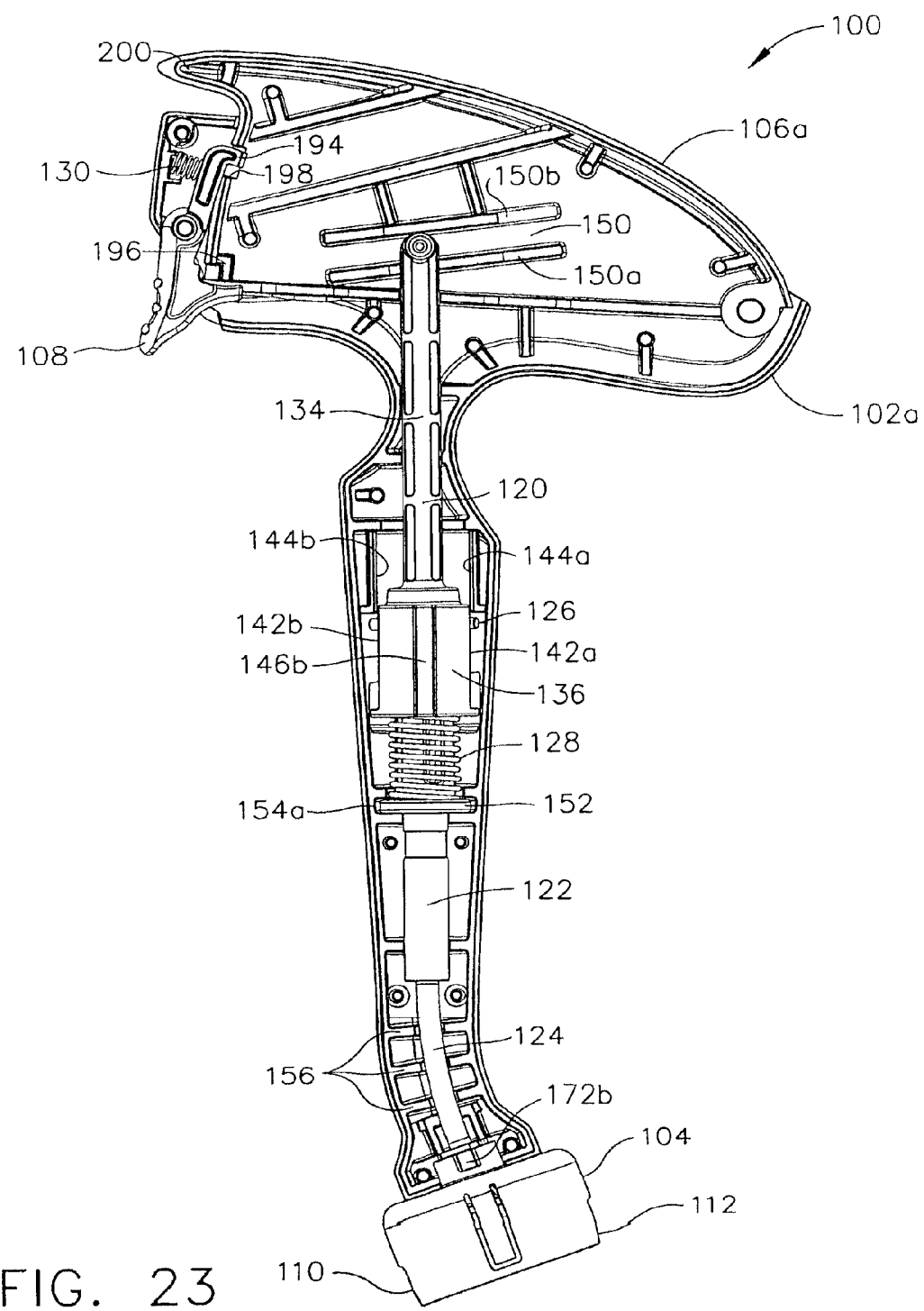
FIG. 23 is a side view of the applier of FIG. 20 similar to FIG. 22, showing the internal components in the applied, actuated position.
Figure 24:
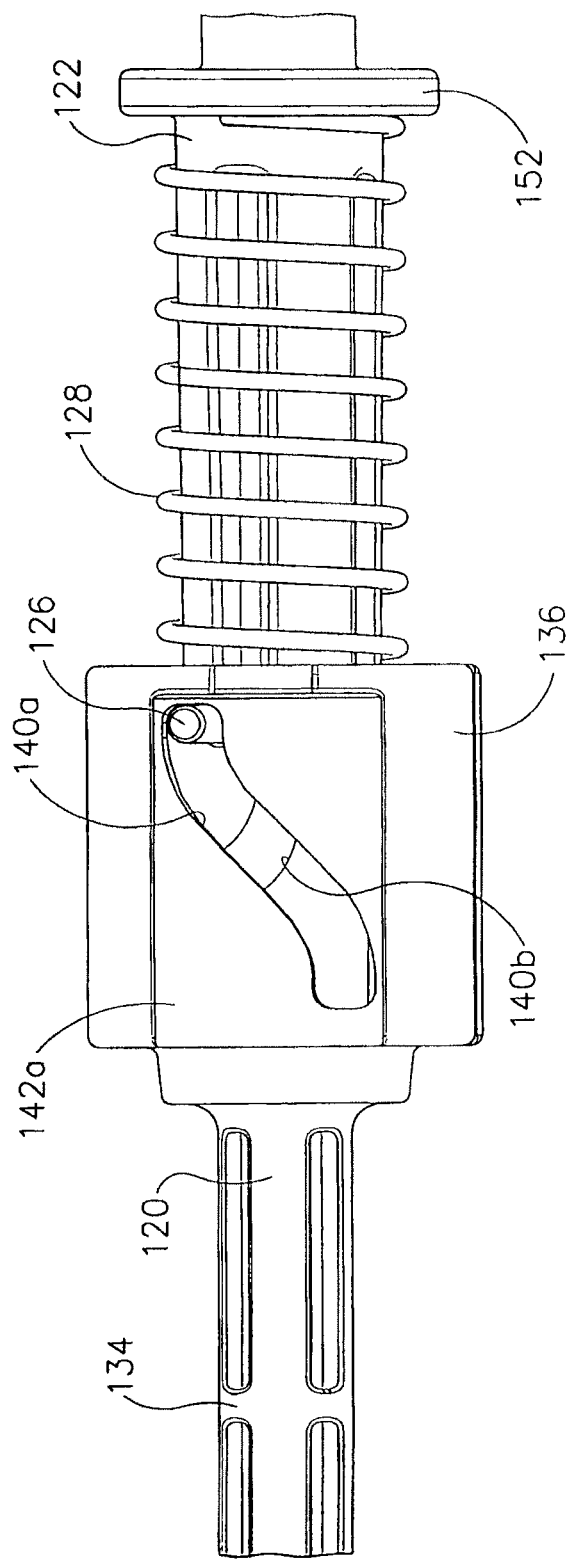
FIG. 24 is an enlarged, fragmentary side view of the linear to rotary cam mechanism of the applier of FIG. 20.
Figure 25:
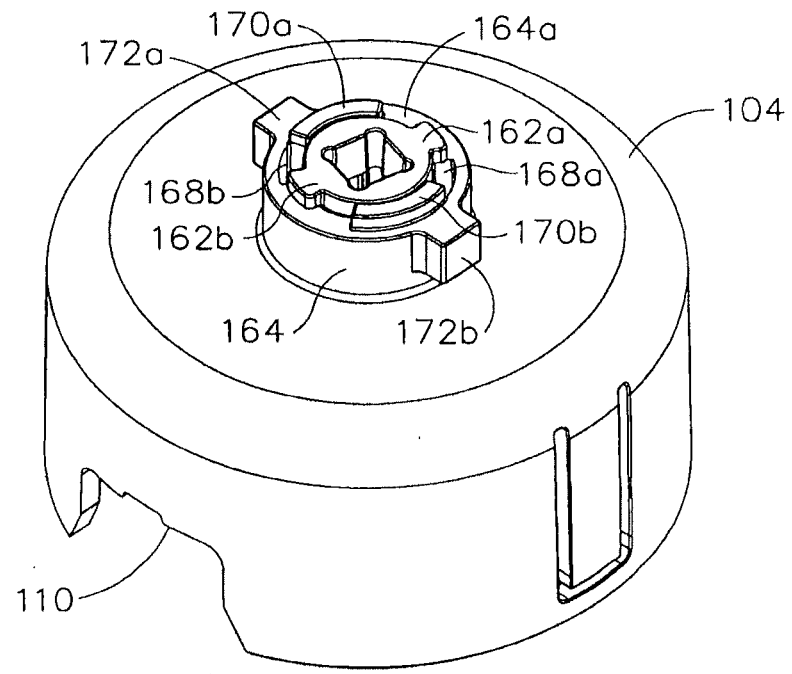
FIG. 25 is an enlarged top perspective view of the locator of the applier of FIG. 20.

Referring also to FIGS. 20 and 22, to insert injection port 2 into locator 104, actuator 106 is oriented in the undeployed position so that actuator 132 is in the undeployed position. Actuator 12 is oriented in the undeployed position, and inserted into locator 104, with extension housing 78 and tab 96 disposed in slots 110 and 112, respectively.

Actuator 106 may, as illustrated in FIG. 20, include a visual indicator to indicate whether actuator 106 is fully in the undeployed state, such as unlocked lock icon 190, and indicia to indicate whether actuator 106 is in the deployed state, such as locked lock icon 192. Such visual indication may be include by any suitable manner, such as by molding integral with actuator 106, applying as a adhesive film or such, or printing directly on actuator 106. With the indicator illustrated, unlocked lock icon 190 is visible adjacent the upper edge of body 102, although other configurations of indication may be utilized, such as a window or such formed in body 102 to reveal the indicia.

To use, locator 104 and a portion of 102, if necessary, is inserted through an incision by the surgeon and located in the desired position adjacent the body tissue to which the medical implant (which in the embodiment depicted is an injection port 2) is to be attached. The angle between locator 104 and body 102 allows the surgeon to visualize the site directly. With injection port 2 in position, the one or more fasteners 10 are moved from the undeployed position to the deployed position in an annular path to engage the tissue. Fasteners 10 allow injection port 2 to be secured to the tissue with a retention strength equal to or greater than when secured with sutures. Safety switch 108 is rotated about pivot pin 118, withdrawing lockout tab 194 from lower opening 196, allowing actuator 106 to be rotated about pivot pin 114. This action causes cam track 150 to move cross member 138 downward, causing cam collar 136 to rotate drive shaft 122, thereby rotating actuator 132 relative to locator 104.

Rotation of actuator 132 actuates actuator 12 by rotating it. The engagement between extension 78 and tab 96 and slots 110 and 112, respectively, prevent port body 8 from rotating, allowing relative motion between actuator 12 and port body 8.

Once actuator 106 reaches the deployed position, lockout tab 194 is urged into upper opening 198, retaining actuator 106 in the deployed position. In the embodiment depicted, spring 130 biases lockout tab 194 sufficiently to produce sound as lockout tab 194 snaps into upper opening 198, providing an audible signal that actuator 106, and therefore actuator 12 and fasteners 10 are deployed fully. As illustrated in FIG. 29, with actuator 106 in the deployed position, actuator 12 has been rotated and fasteners 10 are in the deployed position having penetrated the body tissue, such as the rectus sheath. Cams 178a and 178b have been rotated to a position where surfaces 182a and 182b are adjacent ribs 186a and 186b, with arms 184a and 184b deflected outwardly such that flanges 188a and 188b are not disposed in recesses 56 and not engaging ledges 56a. With injection port 2 secured to the body tissue, and released from locator 104, the surgeon may withdraw locator 104, leaving injection port 2 in place. If a visual indicator of the state of the attachment mechanism is included with the implant, the surgeon can tell whether the attachment mechanism is fully deployed.

The attachment mechanism embodied in injection port 2 is configured to be reversible so that the medical implant, injection port 2, may be moved, such as to reposition it or remove it from the patient. To do so, with actuator 106 in the deployed position, locator 104 is placed over injection port 2, locating extension 78 and tab 96 in slots 110 and 112 so that posts 176a and 176b are engaged with recesses 54. Safety switch 108 is rotated to withdraw lockout tab 194 from upper opening 198, while the surgeon pulls up on extension 200 of actuator 106. Although cam return spring 128 urges cam collar 136 upwardly, extension 200 allows an additional return force to be applied. As cross member 138 is pulled up by cam track 150, actuator 132 rotates actuator 12, moving fasteners 10 from the deployed position to the undeployed position simultaneously, while cams 178a and 178b disengage from ribs 186a and 186b, allowing flanges 188a and 188b to engage recess 56 and ledge 56a so as to retain injection port 2 in locator 104. When actuator 106 has been moved to the undeployed position, lockout tab 194 snaps into lower opening 196, generating an audible signal that actuator 106 is undeployed fully, and injection port 2 is detached from the body tissue and may be relocated or removed.

Figure 30:
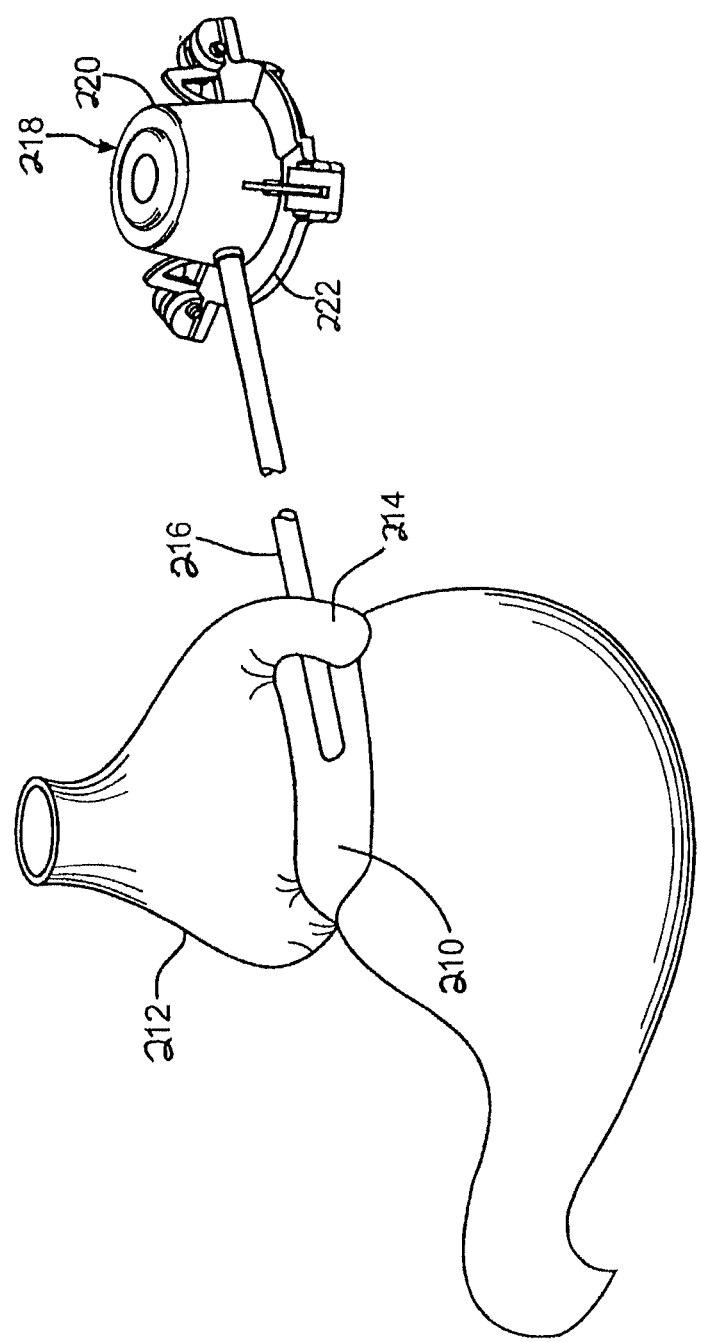
FIG. 30 is a diagrammatic drawing showing an injection port connected to an adjustable gastric band wrapped around an upper part of a stomach.

In FIG. 30, adjustable gastric band 210 is shown wrapped around an upper portion of stomach 212, kept in place by attaching the two ends together and extending portion 214 of the stomach 212 over adjustable gastric band 210 by suturing portion 214 to the stomach. One end of flexible conduit 216 is in fluid communication with the internal cavity of the balloon (not shown), with the other end being in fluid communication with an internal cavity of injection port 218. At the time adjustable gastric band 210 is implanted around a portion of the stomach, remote injection port 218 is also implanted at a suitable location, usually within the rectus sheaths, for transcutaneous access via a Huber needle.

In summary, numerous benefits have been described which result from employing the concepts of the invention. The foregoing description of one or more embodiments of the invention has been presented for purposes of illustration and description. It is not intended to be exhaustive or to limit the invention to the precise form disclosed. Modifications or variations are possible in light of the above teachings. The one or more embodiments were chosen and described in order to illustrate the principles of the invention and its practical application to thereby enable one of ordinary skill in the art to utilize the invention in various embodiments and with various modifications as are suited to the particular use contemplated. It is intended that the scope of the invention be defined by the claims submitted herewith.

We claim:
1. An injection port system, comprising:
 (a) an injection port, wherein the injection port comprises:
  (i) a body, the body having an applier engagement portion, and
  (ii) a plurality of fasteners integral with the body, wherein the plurality of fasteners are movable from a non-deployed position to a deployed position; and
 (b) an applier removably coupled with the injection port, wherein the applier comprises:

(i) a port engagement portion configured to selectively engage the applier engagement portion of the port body to retain the injection port relative to the applier, and (ii) an actuator operable to move the fasteners from the non-deployed position to the deployed position, wherein the applier is configured to disengage the port engagement portion from the applier engagement portion to release the injection port from the applier when the actuator moves the fasteners from the non-deployed position to the deployed position.

2. The injection port system of claim 1, wherein the port engagement portion comprises a resilient member.

3. The injection port system of claim 2, wherein the resilient member is biased to engage the applier engagement portion.

4. The injection port system of claim 1, wherein the port engagement portion comprises an inwardly extending member configured to move from a first position to a second position, wherein the port engagement portion is configured to retain the injection port relative to the applier when the inwardly extending member is in the first position.

5. The injection port system of claim 4, wherein the port engagement portion is configured to release the injection port from the applier when the inwardly extending member is in the second position.

6. The injection port system of claim 5, wherein the applier further comprises a cam, wherein the cam is configured to move the inwardly extending member from the first position to the second position when the actuator moves the fasteners from the non-deployed position to the deployed position.

7. The injection port system of claim 6, wherein the cam is integral with the actuator.

8. The injection port system of claim 7, wherein the actuator is rotatable relative to the port engagement portion, wherein the actuator is operable to rotatably position the cam to a position where the cam moves the inwardly extending member from the first position to the second position.

9. The injection port system of claim 6, wherein the port engagement portion further comprises a cantilever arm, the cantilever arm having a first end and a second end, wherein the inwardly extending member extends inwardly from the first end of the cantilever arm.

10. The injection port system of claim 9, wherein the port engagement portion further comprises a cam engagement feature, wherein the cam engagement feature is positioned at the second end of the cantilever arm, wherein the cam is configured to selectively engage the cam engagement feature.

11. The injection port system of claim 6, wherein the cam is configured to move the inwardly extending member outwardly in order to move the inwardly extending member from the first position to the second position when the actuator moves the fasteners from the non-deployed position to the deployed position.

12. The injection port system of claim 1, wherein the body comprises an inwardly extending recess.

13. The injection port system of claim 12, wherein the applier engagement portion is defined at least in part by the inwardly extending recess, such that the port engagement portion is configured to selectively engage the inwardly extending recess.

14. An injection port applier, wherein the injection port applier comprises:

(a) an elongate shaft having a first end and a second end; and (b) a port engagement feature located at the second end of the elongate shaft, wherein the port engagement feature comprises:

(i) a resilient member movable between a first position and a second position, wherein the resilient member is configured to retain an injection port relative to the port engagement feature when the resilient member is in the first position, wherein the resilient member is configured to release an injection port from the port engagement feature when the resilient member is in the second position, and (ii) an actuator movable from a first position to a second position, wherein the actuator is configured to actuate fasteners of an injection port when the actuator is moved from the first position to the second position, wherein the actuator is further configured to move the resilient member from the first position to the second position when the actuator is moved from the first position to the second position.

15. The injection port applier of claim 14, further comprising an actuating member located at the first end of the elongate shaft, wherein the actuating member is in communication with the actuator, wherein the actuating member is operable to move the actuator from the first position to the second position.

16. The injection port applier of claim 14, wherein the resilient member is resiliently biased to the first position.

17. A method of deploying an injection port using a port applier, wherein the injection port comprises a port body and a plurality of fasteners, wherein the fasteners are movable from a non-deployed position to a deployed position, wherein the port applier comprises a port engagement feature and an actuator, wherein the port engagement feature comprises a resilient member configured to selectively engage the port body, wherein the actuator is operable to move the fasteners from the non-deployed position to the deployed position, the method comprising:

(a) moving the injection port and the port applier to a site in a patient, wherein the injection port is coupled with the port applier and retained by the resilient member during at least part of the act of moving the injection port and the port applier to a site in a patient;

(b) moving the actuator to deploy the fasteners in tissue at the site in the patient; and (c) releasing the port body from the port applier, wherein the act of releasing the port body from the port applier comprises moving the resilient member away from the port body;

wherein the act of moving the actuator to deploy the fasteners and the act of releasing the port body from the port applier are performed substantially simultaneously.

* * * * *